US007442550B1

(12) United States Patent
Mallet et al.

(10) Patent No.: US 7,442,550 B1
(45) Date of Patent: Oct. 28, 2008

(54) METHOD FOR DETECTING THE EXPRESSION OF AN ENVELOPE PROTEIN OF A HUMAN ENDOGENOUS RETROVIRUS AND USES OF A GENE CODING FOR SAID PROTEIN

(75) Inventors: Francois Mallet, Villeurbanne (FR); Francois-Loic Cosset, Lyons (FR); Jean-Luc Blond, Lyons (FR); Dimitri Lavillette, Bercenay le Hay (FR); Olivier Bouton, Francheville (FR); Alessia Ruggieri, Mulhouse (FR)

(73) Assignees: Biomerieux, Marcy l'Etoile (FR); Institut National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 10/069,883

(22) PCT Filed: Sep. 1, 2000

(86) PCT No.: PCT/FR00/02429

§ 371 (c)(1),
(2), (4) Date: May 1, 2002

(87) PCT Pub. No.: WO01/16171

PCT Pub. Date: Mar. 8, 2001

(30) Foreign Application Priority Data

Sep. 1, 1999 (FR) ................................. 99 11141
Sep. 15, 1999 (FR) ................................. 99 11793

(51) Int. Cl.
*C12N 15/02* (2006.01)
*C12P 21/00* (2006.01)
*C12N 15/00* (2006.01)

(52) U.S. Cl. .................. 435/449; 435/70.2; 435/325; 435/339.1; 435/173.4; 435/69.6; 435/70.1

(58) Field of Classification Search .................. 435/6, 435/7.2, 7.21, 7.24, 320.1, 440, 69.1; 424/184.1, 424/187.1; 530/350, 300
See application file for complete search history.

(56) References Cited

U.S. PATENT DOCUMENTS 6,312,921 B1 * 11/2001 Jacobs et al. ............... 435/69.1

FOREIGN PATENT DOCUMENTS

| WO | WO 99/02696 | 1/1999 |
| WO | WO 99/26972 | 6/1999 |
| WO | WO 99/60020 | 11/1999 |

OTHER PUBLICATIONS

Tebit et al. Aids Research and Human Retroviruses 2002, vol. 18 No. 10, pp. 39-48.*
Pancino et al. J Virol. 1995, vol. 69, No. 4, pp. 2110-2118.*
Stephens et al. Science 1998, vol. 282, pp. 754-759.*
Alliel et al. C.R. Acad. Sci. III, 1998, vol. 321, No. 10, pp. 857-863.*
Feit et al. 2003, J. Pat. Trade. Off. Soc., vol. 85, No. 1, pp. 5-21.*
Castagna et al. The J. Experiment. Biol. 1997, vol. 200, pp. 269-286.*
Rasko et al. Proc. Natl. Acad. Sci. USA, Mar. 1999, vol. 96, pp. 2129-2134.*
Tailor et al. J. Virol. Mar. 1999, vol. 73, No. 5, pp. 4470-4474.*
Blond et al. J. Virol. Feb. 1999, vol. 73, No. 2, pp. 1175-1185.*
Blond et al. J. Virol. Apr. 2000, vol. 74, No. 7, pp. 3321-3329.*
Sakomoto et al. J. Virol. methods 2003, vol. 114, pp. 159-166.*
National Library of Medicine-Medical Subject Headings, Feb. 26, 2007.*
J.J. Skehel et al., "Changes in the Conformation of Influenza Virus Hemmagglutinin at the pH Optimum of Virus-Mediated Membrane Fusion," *Proc. Natl. Acad. Sci. USA*, vol. 79, pp. 968-972, Feb. 1982.
J.S. Jones et al., "Cell Fusion Induced by the Murine Leukemia Virus Envelope Glycoprotein," *Journal of Virology*, vol. 67, No. 1, pp. 67-74, Jan. 1993.
P.J.W. Venables et al., "Abundance of an Endogenous Retroviral Envelope Protein in Placental Trophoblasts Suggests A Biological Function," *Virology*, 211, pp. 589-592, 1995.
N. de Parseval et al., "Physiological Knockout of the Envelope Gene of the Single-Copy ERV-3 Human Endogenous Retrovirus in a Fraction of the Caucasian Population," *Journal of Virology*, vol. 72, No. 4, pp. 3442-3445, Apr. 1998.
D. Ott et al., "Sequence Analysis of Amphotropic and 10A1 Murine Leukemia Viruses: Close Relationship to Mink Cell Focus-Inducing Viruses," *Journal of Virology*, vol. 64, No. 2, pp. 757-766, Feb. 1990.
G. Kohler et al., "Continuous Cultures of Fused Cells Secreting Antibody of Predefined Specificity," *Nature*, vol. 256, pp. 495-497, Aug. 1975.
G. Galfre et al., "Antibodies to Major Histocompatibility Antigens Produced by Hybrid Cell Lines," *Nature*, vol. 266, pp. 550-552, Apr. 1977.
A. Roda et al., "Production of High-Titer Antibody to Bile Acids," *Journal of Steroid Biochemistry*, vol. 13, pp. 449-454, 1980.
B.R. Blazar et al., "Anti-CD3∈F(ab')$_2$ Fragments Inhibit T Cell Expansion in Vivo During Graft-Versus-Host Disease or the Primary Immune Response to Nominal Antigen[1,2]," *The Journal of Immunology*, vol. 159, pp. 5821-5833, 1997.

(Continued)

*Primary Examiner*—Bruce R. Campell
*Assistant Examiner*—Bao Qun Li
(74) *Attorney, Agent, or Firm*—Oliff & Berridge, PLC

(57) ABSTRACT

A method for detecting the expression of a polypeptide in cells and for detecting the interaction between a polypeptide and cells, ex vivo or in vitro, wherein the polypeptide is selected from the group consisting of: a peptide comprising the cyt domain of the envelope protein of the human endogenous retrovirus, HERV-W; a peptide comprising amino acids 448-538 of SEQ ID NO: 1; and a peptide comprising a sequence having, for any series of 20 amino acids, at least 80% identity with amino acids 448-538 of SEQ ID NO: 1. Detection is established by the fusogenic power of the polypeptide, which is demonstrated by syncytia formation.

13 Claims, 6 Drawing Sheets

OTHER PUBLICATIONS

R.E. Bird et al., "Single-Chain Antigen-Binding Proteins," *Science*, vol. 242, pp. 423-426, Oct. 1988.

F. Arakawa et al., "Cloning and Sequencing of the $V_H$ and $V_x$ Genes of an Anti-CD3 Monoclonal Antibody, and Construction of a Mouse/Human Chimeric Antibody," *J. Biochem.* vol. 120, No. 3, pp. 657-662, 1996.

V.K. Chaudhary et al., "A Recombinant Immunotoxin Consisting of Two Antibody Variable Domains Fused to *Pseudomonas* Exotoxin," *Nature*, vol. 339, pp. 394-397, Jun. 1989.

F. Cosset et al., "High-Titer Packaging Cells Producing Recombinant Retroviruses Resistant to Human Serum" *Journal of Virology*, vol. 69, No. 12, pp. 7430-7436, Dec. 1995.

Y. Takeuchi et al., "Type C Retrovirus Inactivation by Human Complement is Determined by both the Viral Genome and the Producer Cell," *Journal of Virology*, vol. 68, No. 12, pp. 8001-8007, Dec. 1994.

A. Rein et al., "Function of the Cytoplasmic Doman of a Retroviral Transmembrane Protein: p15E-p2E Cleavage Activates the Membrane Fusion Capability of the Murine Leukemia Virus Env Protein," Journal of Virology, vol. 68, No. 3, pp. 1773-1781, Mar. 1994.

F. Cosset et al., "Retroviral Retargeting by Envelopes Expressing an N-Terminal Binding Domain," *Journal of Virology*, vol. 69, No. 10, pp. 6314-6322, Oct. 1995.

S. Yant et al., "Identification of Cytoplasmic Tyr-X-X-Leu Motif Essential for Down Regulation of the Human Cell Receptor CD46 in Persistent Measles Virus Infection," *Journal of Virology*, vol. 71, No. 1, pp. 766-770, Jan. 1997.

J. Blond et al., "Molecular Characterization and Placental Expression of HERV-W, a New Human Endogenous Retrovirus Family," *Journal of Virology*, vol. 73, No. 2, pp. 1175-1185, Feb. 1999.

C.S. Tailor et al., "A Sodium-Dependent Neutral-Amino-Acid Transporter Mediates Infections of Feline and Baboon Endogenous Retroviruses and Simian Type D Retroviruses," *Journal of Virology*, vol. 73, No. 5, pp. 4470-4474, May 1999.

J.E.J. Rasko et al., "The RD114/Simian Type D Retrovirus Receptor is a Neutral Amino Acid Transporter," *Proc. Natl. Acad. Sci. USA*, vol. 96, pp. 2129-2134, Mar. 1999.

B. Wang et al., "Molecular Cloning, Expression, and Biological Characterization of an HTLV-II Envelope Glycoprotein: HIV-1 Expression Is Permissive for HTLV-II-Induced Cell Fusion," *Aids Research and Human Retroviruses*, Vo. 9, No. 9, pp. 849-860, 1993.

L. Lin et al., "Expression of Endogenous Retrovirus ERV-3 Induces Differentiation in BeWo, a Choriocarcinoma Model Of Human Placental Trophoblast," *Placenta*, vol. 20, No. 1, pp. 109-118, Jan. 1999.

B.J. Doranz et al., "A Small-Molecule Inhibitor Directed Against the Chemokine Receptor CXCR4 Prevents its use as an HIV-1 Coreceptor," *Journal of Experimental Medicine*, vol. 186, No. 8, pp. 1395-1400, Oct. 1997.

N.E. Avissar et al., "Characterization of Antibodies to Intestinal $NA^+$ Dependent Neural Amino Acid Transporter ($B^0$)," *Gastroenterology*, vol. 118, No. 4, Apr. 2000.

C. Voisset et al., "Chromosomal Distribution and Coding Capacity of the Human Endogenous Retrovirus HERV-W Family," *Aids Research and Human Retroviruses*, vol. 16, No. 8, pp. 731-740, May 2000.

S. Mi et al., "Syncytin is a Captive Retroviral Envelope Protein Involved in Human Placental Morphogenesis," *Nature*, vol. 403, No. 6771, pp. 785-789, Apr. 2000.

* cited by examiner

| Construct | Fusion |
|---|---|
| HERV-W | +++ |
| CD46 | - |
| W/CD46+ | - |
| MLV-A | - |
| W/R+ | - |
| RD114 | - |
| RD/W | +++ |

Scheme and characterization of the chimeric Env HERV-Ws

SEQUENCE LISTING

<160> NUMBER OF SEQ ID NOS: 64

<210> SEQ ID NO 1
<211> LENGTH: 538
<212> TYPE: PRT
<213> ORGANISM: Homo sapiens

<400> SEQUENCE: 1

```
Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
            35                  40                  45

Ala Pro Ser Tyr Arg Ser Leu Ser Lys Gly Thr Pro Thr Phe Thr Ala
        50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Gly Val Gln Asp Gln Ala Arg Glu Lys His
            115                 120                 125

Val Lys Glu Val Ile Ser Gln Leu Thr Arg Val His Gly Thr Ser Ser
        130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
            195                 200                 205

Phe Ser Thr Glu Ile Asn Thr Thr Ser Val Leu Val Gly Pro Leu Val
            210                 215                 220
```

```
Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
            245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Ala Val Val Leu Gln Asn Arg Arg
    370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Pro Ala Ser Pro Arg Ser Asp Val
            500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
    530                 535

<210> SEQ ID NO 2
<211> LENGTH: 2781
<212> TYPE: DNA
<213> ORGANISM: Homo sapiens

<400> SEQUENCE: 2
atgggagctg ttttcatgct atttcactct attaaatctt gcaactgcac tcttctggtc      60
catgtttctt acggctcgag ctgagctttt gctcaccgtc caccactgct gtttgccacc     120
accgcagacc tgccgctgac tcccatccct ctggatcctg cagggtgtcc gctgtgctcc     180
tgatccagcg aggcgcccat gccgctcccc aattgggcta aaggcttgcc attgttcctg     240
cacggctaag tgcctgggtt tgttctaatt gagctgaaca ctagtcactg ggttccatgg     300
ttctcttctg tgacccacgg cttctaatag aactataaca cttaccacat ggcccaagat     360
```

```
tccattcctt ggaatccgtg aggccaagaa ctccaggtca gagaatacga ggcttgccac    420
catcttggaa gcggcctgct accatcttgg aagtggttca ccaccatctt gggagctctg    480
tgagcaagga ccccccggta acattttggc aaccacgaac ggacatccaa agtgatacat    540
cctgggaagg accctaccca gtcatttat  ctaccccaac tgcggttaaa gtggctggag    600
tggagtcttg gatacatcac acttgagtca atcctggat  actgccaaag gaacctgaaa    660
atccaggaga caacgctagc tattcctgtg aacctctaga ggatttgcgc ctgctcttca    720
aacaacaacc aggaggaaag taactaaaat cataaatccc catggccctc ccttatcata    780 ttttctctt  tactgttctt ttaccctctt tcactctcac tgcaccccct ccatgccgct    840
gtatgaccag tagctcccct taccaagagt ttctatggag aatgcagcgt cccggaaata    900
ttgatgcccc atcgtatagg agtctttcta agggaacccc caccttcact gcccacaccc    960
atatgccccg caactgctat cactctgcca ctctttgcat gcatgcaaat actcattatt    1020
ggacaggaaa aatgattaat cctagttgtc ctggaggact tggagtcact gtctgttgga    1080
cttacttcac ccaaactggt atgtctgatg ggggtggagt tcaagatcag gcaagagaaa    1140
aacatgtaaa agaagtaatc tcccaactca cccgggtaca tggcacctct agcccctaca    1200
aaggactaga tctctcaaaa ctacatgaaa ccctccgtac ccatactcgc tggtaagcc     1260 tatttaatac caccctcact gggctccatg aggtctcggc ccaaaaccct actaactgtt    1320
ggatatgcct cccctgaac  ttcaggccat atgtttcaat ccctgtacct gaacaatgga    1380
acaacttcag cacagaaata aacaccactt ccgttttagt aggacctctt gtttccaatc    1440
tggaaataac ccatacctca aacctcacct gtgtaaaatt tagcaatact acatacacaa    1500
ccaactccca atgcatcagg tgggtaactc ctcccacaca aatagtctgc ctaccctcag    1560 gaatatttt  tgtctgtggt acctcagcct atcgttgttt gaatggctct tcagaatcta    1620
tgtgcttcct ctcattctta gtgcccccta tgaccatcta cactgaacaa gatttataca    1680
gttatgtcat atctaagccc cgcaacaaaa gagtacccat tcttcctttt gttataggag    1740
cgggagtgct aggtgcacta ggtactggca ttggcggtat cacaacctct actcagttct    1800
actacaaact atctcaagaa ctaaatgggg acatggaacg ggtcgccgac tccctggtca    1860
ccttgcaaga tcagcttaac tccctagcag cagtagtcct tcaaaatcga agagctttag    1920
acttgctaac cgctgaaaga gggggaacct gtttattttt aggggaagaa tgctgttatt    1980
atgttaatca atccggaatc gtcactgaga aagttaaaga aattcgagat cgaatacaac    2040
gtagagcaga ggagcttcga aacactggac cctggggcct cctcagccaa tggatgccct    2100
ggattctccc cttcttagga cctctagcag ctataatatt gctactcctc tttggaccct    2160
gtatctttaa cctccttgtt aactttgtct cttccagaat cgaagctgta aaactacaaa    2220
tggagcccaa gatgcagtcc aagactaaga tctaccgcag accccctggac cggcctgcta    2280 gcccacgatc tgatgttaat gacatcaaag gcacccctcc tgaggaaatc tcagctgcac    2340
aacctctact acgccccaat tcagcaggaa gcagttagag cggtcgtcgg ccaacctccc    2400
caacagcact taggttttcc tgttgagatg ggggactgag agacaggact agctggattt    2460
cctaggctga ctaagaatcc ctaagcctag ctgggaaggt gaccacatcc acctttaaac    2520 acgggcttg  caacttagct cacacctgac caatcagaga gctcactaaa atgctaatta    2580
ggcaaagaca ggaggtaaag aaatagccaa tcatctattg cctgagagca cagcaggagg    2640
gacaatgatc gggatataaa cccaagtctt cgagccggca acggcaaccc cctttgggtc    2700
```

```
ccctcccttt gtatgggagc tctgttttca tgctatttca ctctattaaa tcttgcaact    2760
gcaaaaaaaa aaaaaaaaaa a                                              2781

<210> SEQ ID NO 3
<211> LENGTH: 28
<212> TYPE: DNA
<213> ORGANISM: Homo sapiens

<400> SEQUENCE: 3
caaaacgcct ggagatacag caattatc                                       28

<210> SEQ ID NO 4
<211> LENGTH: 25
<212> TYPE: DNA
<213> ORGANISM: Homo sapiens

<400> SEQUENCE: 4
gcaccctcat ggttgtgtta cttgg                                          25

<210> SEQ ID NO 5
<211> LENGTH: 26
<212> TYPE: DNA
<213> ORGANISM: Homo sapiens

<400> SEQUENCE: 5
ctgaaaatcc aggagacaac gctagc                                         26

<210> SEQ ID NO 6
<211> LENGTH: 25
<212> TYPE: DNA
<213> ORGANISM: Homo sapiens

<400> SEQUENCE: 6
gcaccctcat ggttgtgtta cttgg                                          25

<210> SEQ ID NO 7
<211> LENGTH: 36
<212> TYPE: DNA
<213> ORGANISM: Homo sapiens

<400> SEQUENCE: 7
ttggtaccca aaacgcctgg agatacagca attatc                              36

<210> SEQ ID NO 8
<211> LENGTH: 29
<212> TYPE: DNA
<213> ORGANISM: Homo sapiens

<400> SEQUENCE: 8
aactcgagtg aaatagcatg aaaacagag                                      29

<210> SEQ ID NO 9
<211> LENGTH: 25
<212> TYPE: DNA
<213> ORGANISM: Homo sapiens

<400> SEQUENCE: 9
aggaaagtaa ctaaaatcat aaatc                                          25

<210> SEQ ID NO 10
<211> LENGTH: 20
<212> TYPE: DNA
<213> ORGANISM: Homo sapiens
```

```
<400> SEQUENCE: 10
ggttccctta gaaagactcc                                                    20

<210> SEQ ID NO 11
<211> LENGTH: 22
<212> TYPE: DNA
<213> ORGANISM: Homo sapiens

<400> SEQUENCE: 11
aatattgatg ccccatcgta ta                                                 22

<210> SEQ ID NO 12
<211> LENGTH: 21
<212> TYPE: DNA
<213> ORGANISM: Homo sapiens

<400> SEQUENCE: 12
ccagtttggg tgaagtaagt c                                                  21

<210> SEQ ID NO 13
<211> LENGTH: 21
<212> TYPE: DNA
<213> ORGANISM: Homo sapiens

<400> SEQUENCE: 13
ggaggacttg gagtcactgt c                                                  21

<210> SEQ ID NO 14
<211> LENGTH: 20
<212> TYPE: DNA
<213> ORGANISM: Homo sapiens

<400> SEQUENCE: 14
aggcgagtat gggtacggag                                                    20

<210> SEQ ID NO 15
<211> LENGTH: 23
<212> TYPE: DNA
<213> ORGANISM: Homo sapiens

<400> SEQUENCE: 15
ggactagatc tctcaaaact aca                                                23

<210> SEQ ID NO 16
<211> LENGTH: 22
<212> TYPE: DNA
<213> ORGANISM: Homo sapiens

<400> SEQUENCE: 16
acggaagtgg tgtttatttc tg                                                 22

<210> SEQ ID NO 17
<211> LENGTH: 21
<212> TYPE: DNA
<213> ORGANISM: Homo sapiens

<400> SEQUENCE: 17
cctgaacaat ggaacaactt c                                                  21

<210> SEQ ID NO 18
<211> LENGTH: 20
<212> TYPE: DNA
```

<213> ORGANISM: Homo sapiens

<400> SEQUENCE: 18
attcctgagg gtaggcagac 20

<210> SEQ ID NO 19
<211> LENGTH: 20
<212> TYPE: DNA
<213> ORGANISM: Homo sapiens

<400> SEQUENCE: 19
ggtaactcct cccacacaaa 20

<210> SEQ ID NO 20
<211> LENGTH: 21
<212> TYPE: DNA
<213> ORGANISM: Homo sapiens

<400> SEQUENCE: 20
gaatgggtac tcttttgttg c 21

<210> SEQ ID NO 21
<211> LENGTH: 23
<212> TYPE: DNA
<213> ORGANISM: Homo sapiens

<400> SEQUENCE: 21
tacagttatg tcatatctaa gcc 23

<210> SEQ ID NO 22
<211> LENGTH: 22
<212> TYPE: DNA
<213> ORGANISM: Homo sapiens

<400> SEQUENCE: 22
taagttgatc ttgcaaggtg ac 22

<210> SEQ ID NO 23
<211> LENGTH: 20
<212> TYPE: DNA
<213> ORGANISM: Homo sapiens

<400> SEQUENCE: 23
ctaaatgggg acatggaacg 20

<210> SEQ ID NO 24
<211> LENGTH: 24
<212> TYPE: DNA
<213> ORGANISM: Homo sapiens

<400> SEQUENCE: 24
tattcgatct ggaatttctt caac 24

<210> SEQ ID NO 25
<211> LENGTH: 20
<212> TYPE: DNA
<213> ORGANISM: Homo sapiens

<400> SEQUENCE: 25
caatccggaa tcgtcactga 20

<210> SEQ ID NO 26
<211> LENGTH: 23

```
<212> TYPE: DNA
<213> ORGANISM: Homo sapiens

<400> SEQUENCE: 26
agacaaagtt aacaaggagg ttc                                         23

<210> SEQ ID NO 27
<211> LENGTH: 22
<212> TYPE: DNA
<213> ORGANISM: Homo sapiens

<400> SEQUENCE: 27
actcctcttt ggaccctgta tc                                          22

<210> SEQ ID NO 28
<211> LENGTH: 18
<212> TYPE: DNA
<213> ORGANISM: Homo sapiens

<400> SEQUENCE: 28
gaggttggcc gaccaccg                                               18

<210> SEQ ID NO 29
<211> LENGTH: 28
<212> TYPE: DNA
<213> ORGANISM: Artificial Sequence
<220> FEATURE:
<223> OTHER INFORMATION: primer U6198

<400> SEQUENCE: 29
caaaacgcct ggagatacag caattatc                                    28

<210> SEQ ID NO 30
<211> LENGTH: 25
<212> TYPE: DNA
<213> ORGANISM: Artificial Sequence
<220> FEATURE:
<223> OTHER INFORMATION: primer L6186

<400> SEQUENCE: 30
gcaccctcat ggttgtgtta cttgg                                       25

<210> SEQ ID NO 31
<211> LENGTH: 26
<212> TYPE: DNA
<213> ORGANISM: Artificial Sequence
<220> FEATURE:
<223> OTHER INFORMATION: primer U6189

<400> SEQUENCE: 31
ctgaaaatcc aggagacaac gctagc                                      26

<210> SEQ ID NO 32
<211> LENGTH: 36
<212> TYPE: DNA
<213> ORGANISM: Artificial Sequence
<220> FEATURE:
<223> OTHER INFORMATION: primer U6460

<400> SEQUENCE: 32
ttggtaccca aaacgcctgg agatacagca attatc                           36

<210> SEQ ID NO 33
<211> LENGTH: 29
<212> TYPE: DNA
```

```
<213> ORGANISM: Artificial Sequence
<220> FEATURE:
<223> OTHER INFORMATION: primer L5643

<400> SEQUENCE: 33
aactcgagtg aaatagcatg aaaacagag                                      29

<210> SEQ ID NO 34
<211> LENGTH: 25
<212> TYPE: DNA
<213> ORGANISM: Artificial Sequence
<220> FEATURE:
<223> OTHER INFORMATION: primer U6302

<400> SEQUENCE: 34
aggaaagtaa ctaaaatcat aaatc                                          25

<210> SEQ ID NO 35
<211> LENGTH: 20
<212> TYPE: DNA
<213> ORGANISM: Artificial Sequence
<220> FEATURE:
<223> OTHER INFORMATION: primer L6303

<400> SEQUENCE: 35 ggttcccttagaaagactcc                                                 20

<210> SEQ ID NO 36
<211> LENGTH: 22
<212> TYPE: DNA
<213> ORGANISM: Artificial Sequence
<220> FEATURE:
<223> OTHER INFORMATION: primer U6304

<400> SEQUENCE: 36
aatattgatg ccccatcgta ta                                             22

<210> SEQ ID NO 37
<211> LENGTH: 21
<212> TYPE: DNA
<213> ORGANISM: Artificial Sequence
<220> FEATURE:
<223> OTHER INFORMATION: primer L6305

<400> SEQUENCE: 37
ccagtttggg tgaagtaagt c                                              21

<210> SEQ ID NO 38
<211> LENGTH: 21
<212> TYPE: DNA
<213> ORGANISM: Artificial Sequence
<220> FEATURE:
<223> OTHER INFORMATION: primer U6306

<400> SEQUENCE: 38
ggaggacttg gagtcactgt c                                              21

<210> SEQ ID NO 39
<211> LENGTH: 20
<212> TYPE: DNA
<213> ORGANISM: Artificial Sequence
<220> FEATURE:
<223> OTHER INFORMATION: primer L6307

<400> SEQUENCE: 39
aggcgagtat gggtacggag                                                20
```

<210> SEQ ID NO 40
<211> LENGTH: 23
<212> TYPE: DNA
<213> ORGANISM: Artificial Sequence
<220> FEATURE:
<223> OTHER INFORMATION: primer U6308

<400> SEQUENCE: 40
ggactagatc tctcaaaact aca                                    23

<210> SEQ ID NO 41
<211> LENGTH: 22
<212> TYPE: DNA
<213> ORGANISM: Artificial Sequence
<220> FEATURE:
<223> OTHER INFORMATION: primer L6309

<400> SEQUENCE: 41
acggaagtgg tgtttatttc tg                                     22

<210> SEQ ID NO 42
<211> LENGTH: 21
<212> TYPE: DNA
<213> ORGANISM: Artificial Sequence
<220> FEATURE:
<223> OTHER INFORMATION: primer U6310

<400> SEQUENCE: 42
cctgaacaat ggaacaactt c                                      21

<210> SEQ ID NO 43
<211> LENGTH: 20
<212> TYPE: DNA
<213> ORGANISM: Artificial Sequence
<220> FEATURE:
<223> OTHER INFORMATION: primer L6311

<400> SEQUENCE: 43
attcctgagg gtaggcagac                                        20

<210> SEQ ID NO 44
<211> LENGTH: 20
<212> TYPE: DNA
<213> ORGANISM: Artificial Sequence
<220> FEATURE:
<223> OTHER INFORMATION: primer U6312

<400> SEQUENCE: 44
ggtaactcct cccacacaaa                                        20

<210> SEQ ID NO 45
<211> LENGTH: 21
<212> TYPE: DNA
<213> ORGANISM: Artificial Sequence
<220> FEATURE:
<223> OTHER INFORMATION: primer L6313

<400> SEQUENCE: 45
gaatgggtac tcttttgttg c                                      21

<210> SEQ ID NO 46
<211> LENGTH: 23
<212> TYPE: DNA
<213> ORGANISM: Artificial Sequence
<220> FEATURE:

<223> OTHER INFORMATION: primer U6314

<400> SEQUENCE: 46
tacagttatg tcatatctaa gcc                                    23

<210> SEQ ID NO 47
<211> LENGTH: 22
<212> TYPE: DNA
<213> ORGANISM: Artificial Sequence
<220> FEATURE:
<223> OTHER INFORMATION: primer L6315

<400> SEQUENCE: 47
taagttgatc ttgcaaggtg ac                                     22

<210> SEQ ID NO 48
<211> LENGTH: 20
<212> TYPE: DNA
<213> ORGANISM: Artificial Sequence
<220> FEATURE:
<223> OTHER INFORMATION: primer U6316

<400> SEQUENCE: 48
ctaaatgggg acatggaacg                                        20

<210> SEQ ID NO 49
<211> LENGTH: 24
<212> TYPE: DNA
<213> ORGANISM: Artificial Sequence
<220> FEATURE:
<223> OTHER INFORMATION: primer L6317

<400> SEQUENCE: 49
tattcgatct ggaatttctt caac                                   24

<210> SEQ ID NO 50
<211> LENGTH: 20
<212> TYPE: DNA
<213> ORGANISM: Artificial Sequence
<220> FEATURE:
<223> OTHER INFORMATION: primer U6318

<400> SEQUENCE: 50
caatccggaa tcgtcactga                                        20

<210> SEQ ID NO 51
<211> LENGTH: 23
<212> TYPE: DNA
<213> ORGANISM: Artificial Sequence
<220> FEATURE:
<223> OTHER INFORMATION: primer L6319

<400> SEQUENCE: 51
agacaaagtt aacaaggagg ttc                                    23

<210> SEQ ID NO 52
<211> LENGTH: 22
<212> TYPE: DNA
<213> ORGANISM: Artificial Sequence
<220> FEATURE:
<223> OTHER INFORMATION: primer U6320

<400> SEQUENCE: 52
actcctcttt ggaccctgta tc                                     22

<210> SEQ ID NO 53
<211> LENGTH: 18
<212> TYPE: DNA
<213> ORGANISM: Artificial Sequence
<220> FEATURE:
<223> OTHER INFORMATION: primer L6321

<400> SEQUENCE: 53
gaggttggcc gaccaccg                                                 18

<210> SEQ ID NO 54
<211> LENGTH: 1617
<212> TYPE: DNA
<213> ORGANISM: Homo sapiens
<220> FEATURE:
<221> NAME/KEY: CDS
<222> LOCATION: (1)..(1614)
<223> OTHER INFORMATION:

<400> SEQUENCE: 54

```
atg gcc ctc cct tat cat att ttt ctc ttt act gtt ctt tta ccc tct      48
Met Ala Leu Pro Tyr His Ile Phe Leu Phe Thr Val Leu Leu Pro Ser
 1               5                  10                  15 ttc act ctc act gca ccc cct cca tgc cgc tgt atg acc agt agc tcc      96
Phe Thr Leu Thr Ala Pro Pro Pro Cys Arg Cys Met Thr Ser Ser Ser
             20                  25                  30 cct tac caa gag ttt cta tgg aga atg cag cgt ccc gga aat att gat     144
Pro Tyr Gln Glu Phe Leu Trp Arg Met Gln Arg Pro Gly Asn Ile Asp
         35                  40                  45 gcc cca tgc tat agg agt ctt tct aag gga acc ccc acc ttc act gcc     192
Ala Pro Cys Tyr Arg Ser Leu Ser Lys Gly Thr Pro Thr Phe Thr Ala
     50                  55                  60 cac acc cat atg ccc cgc aac tgc tat cac tct gcc act ctt tgc atg     240
His Thr His Met Pro Arg Asn Cys Tyr His Ser Ala Thr Leu Cys Met
 65                  70                  75                  80 cat gca aat act cat tat tgg aca gga aaa atg att aat cct agt tgt     288
His Ala Asn Thr His Tyr Trp Thr Gly Lys Met Ile Asn Pro Ser Cys
                 85                  90                  95 cct gga gga ctt gga gtc act gtc tgt tgg act tac ttc acc caa act     336
Pro Gly Gly Leu Gly Val Thr Val Cys Trp Thr Tyr Phe Thr Gln Thr
            100                 105                 110 ggt atg tct gat ggg ggt gga gtt caa gat cag gca aga gaa aaa cat     384
Gly Met Ser Asp Gly Gly Gly Val Gln Asp Gln Ala Arg Glu Lys His
        115                 120                 125 gya aaa gaa gta atc tcc caa ctc acc cgg gta cat ggc acc tct agc     432
Xaa Lys Glu Val Ile Ser Gln Leu Thr Arg Val His Gly Thr Ser Ser
    130                 135                 140 ccc tac aaa gga cta gat ctc tca aaa cta cat gaa acc ctc cgt acc     480
Pro Tyr Lys Gly Leu Asp Leu Ser Lys Leu His Glu Thr Leu Arg Thr
145                 150                 155                 160 cat act cgc ctg gta agc cta ttt aat acc acc ctc act ggg ctc cat     528
His Thr Arg Leu Val Ser Leu Phe Asn Thr Thr Leu Thr Gly Leu His
                165                 170                 175 gag gtc tcg gcc caa aac cct act aac tgt tgg ata tgc ctc ccc ctg     576
Glu Val Ser Ala Gln Asn Pro Thr Asn Cys Trp Ile Cys Leu Pro Leu
            180                 185                 190 aac ttc agg cca tat gtt tca atc cct gta cct gaa caa tgg aac aac     624
Asn Phe Arg Pro Tyr Val Ser Ile Pro Val Pro Glu Gln Trp Asn Asn
        195                 200                 205 ttc agc aca gaa ata aac acc act tcc gtt tta gta gga cct ctt gyt     672
Phe Ser Thr Glu Ile Asn Thr Thr Ser Val Leu Val Gly Pro Leu Xaa
    210                 215                 220
```

```
tcc aat ctg gaa ata acc cat acc tca aac ctc acc tgt gta aaa ttt      720
Ser Asn Leu Glu Ile Thr His Thr Ser Asn Leu Thr Cys Val Lys Phe
225                 230                 235                 240 agc aat act aca tac aca acc aac tcc caa tgc atc agg tgg gta act      768
Ser Asn Thr Thr Tyr Thr Thr Asn Ser Gln Cys Ile Arg Trp Val Thr
                245                 250                 255 cct ccc aca caa ata gtc tgc cta ccc tca gga ata ttt ttt gtc tgt      816
Pro Pro Thr Gln Ile Val Cys Leu Pro Ser Gly Ile Phe Phe Val Cys
            260                 265                 270 ggt acc tca gcc tat cgt tgt ttg aat ggc tct tca gaa tct atg tgc      864
Gly Thr Ser Ala Tyr Arg Cys Leu Asn Gly Ser Ser Glu Ser Met Cys
        275                 280                 285 ttc ctc tca ttc tta gtg ccc cct atg acc atc tac act gaa caa gat      912
Phe Leu Ser Phe Leu Val Pro Pro Met Thr Ile Tyr Thr Glu Gln Asp
    290                 295                 300 tta tac art tat gtc ata tct aag ccc cgc aac aaa aga gta ccc att      960
Leu Tyr Xaa Tyr Val Ile Ser Lys Pro Arg Asn Lys Arg Val Pro Ile
305                 310                 315                 320 ctt cct ttt gtt ata gga gca gga gtg cta ggt gca cta ggt act ggc     1008
Leu Pro Phe Val Ile Gly Ala Gly Val Leu Gly Ala Leu Gly Thr Gly
                325                 330                 335 att ggc ggt atc aca acc tct act cag ttc tac tac aaa cta tct caa     1056
Ile Gly Gly Ile Thr Thr Ser Thr Gln Phe Tyr Tyr Lys Leu Ser Gln
            340                 345                 350 gaa cta aat ggg gac atg gaa cgg gtc gcc gac tcc ctg gtc acc ttg     1104
Glu Leu Asn Gly Asp Met Glu Arg Val Ala Asp Ser Leu Val Thr Leu
        355                 360                 365 caa gat caa ctt aac tcc cta gcg aca gta gtc ctt caa aat cga aga     1152
Gln Asp Gln Leu Asn Ser Leu Ala Thr Val Val Leu Gln Asn Arg Arg
    370                 375                 380 gct tta gac ttg cta acc gct gaa aga ggg gga acc tgt tta ttt tta     1200
Ala Leu Asp Leu Leu Thr Ala Glu Arg Gly Gly Thr Cys Leu Phe Leu
385                 390                 395                 400 ggg gaa gaa tgc tgt tat tat gtt aat caa tcc gga atc gtc act gag     1248
Gly Glu Glu Cys Cys Tyr Tyr Val Asn Gln Ser Gly Ile Val Thr Glu
                405                 410                 415 aaa gtt aaa gaa att cga gat cga ata caa cgt aga gca gag gag ctt     1296
Lys Val Lys Glu Ile Arg Asp Arg Ile Gln Arg Arg Ala Glu Glu Leu
            420                 425                 430 cga aac act gga ccc tgg ggc ctc ctc agc caa tgg atg ccc tgg att     1344
Arg Asn Thr Gly Pro Trp Gly Leu Leu Ser Gln Trp Met Pro Trp Ile
        435                 440                 445 ctc ccc ttc tta gga cct cta gca gct ata ata ttg cta ctc ctc ttt     1392
Leu Pro Phe Leu Gly Pro Leu Ala Ala Ile Ile Leu Leu Leu Leu Phe
    450                 455                 460 gga ccc tgt atc ttt aac ctc ctt gtt aac ttt gtc tct tcc aga atc     1440
Gly Pro Cys Ile Phe Asn Leu Leu Val Asn Phe Val Ser Ser Arg Ile
465                 470                 475                 480 gaa gct gta aaa cta caa atg gag ccc aag atg cag tcc aag act aag     1488
Glu Ala Val Lys Leu Gln Met Glu Pro Lys Met Gln Ser Lys Thr Lys
                485                 490                 495 atc tac cgc aga ccc ctg gac cgg aat gct agc cca cga tct gat gtt     1536
Ile Tyr Arg Arg Pro Leu Asp Arg Asn Ala Ser Pro Arg Ser Asp Val
            500                 505                 510 aat gac atc aaa ggc acc cct cct gag gaa atc tca gct gca caa cct     1584
Asn Asp Ile Lys Gly Thr Pro Pro Glu Glu Ile Ser Ala Ala Gln Pro
        515                 520                 525 cta cta cgc ccc aat tca gca gga agc agt tag                         1617
Leu Leu Arg Pro Asn Ser Ala Gly Ser Ser
    530                 535
```

<210> SEQ ID NO 55
<211> LENGTH: 538
<212> TYPE: PRT
<213> ORGANISM: Homo sapiens
<220> FEATURE:
<221> NAME/KEY: misc_feature
<222> LOCATION: (129)..(129)
<223> OTHER INFORMATION: The 'Xaa' at location 129 stands for Ala, or Val.
<220> FEATURE:
<221> NAME/KEY: misc_feature
<222> LOCATION: (224)..(224)
<223> OTHER INFORMATION: The 'Xaa' at location 224 stands for Ala, or Val.
<220> FEATURE:
<221> NAME/KEY: misc_feature
<222> LOCATION: (307)..(307)
<223> OTHER INFORMATION: The 'Xaa' at location 307 stands for Ser, or Asn.

<400> SEQUENCE: 55

Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser
            20                  25                  30

Pro Tyr Gln Glu Phe Leu Trp Arg Met Gln Arg Pro Gly Asn Ile Asp
        35                  40                  45

Ala Pro Cys Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65              70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
        115                 120                 125

Xaa Lys Glu Val Ile Ser Gln Leu Thr Arg Val His Gly Thr Ser Ser
130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Xaa
    210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp

```
            290                 295                 300
Leu Tyr Xaa Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Thr Val Val Leu Gln Asn Arg Arg
    370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
    450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Asn Ala Ser Pro Arg Ser Asp Val
            500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
    530                 535

<210> SEQ ID NO 56
<211> LENGTH: 1617
<212> TYPE: DNA
<213> ORGANISM: Homo sapiens
<220> FEATURE:
<221> NAME/KEY: CDS
<222> LOCATION: (1)..(1614)
<223> OTHER INFORMATION:

<400> SEQUENCE: 56 atg gcc ctc cct tat cat att ttt ctc ttt act gtt ctt tta ccc tct      48
Met Ala Leu Pro Tyr His Ile Phe Leu Phe Thr Val Leu Leu Pro Ser
1               5                   10                  15 ttc act ctc act gca ccc cct cca tgc cgc tgt atg acc agt agc tcc      96
Phe Thr Leu Thr Ala Pro Pro Pro Cys Arg Cys Met Thr Ser Ser Ser
                20                  25                  30 cct tac caa gag ttt cta tgg aga atg cag cgt ccc gga aat att gat     144
Pro Tyr Gln Glu Phe Leu Trp Arg Met Gln Arg Pro Gly Asn Ile Asp
            35                  40                  45 gcc cca tgc tat agg agt ctt tct aag gga acc ccc acc ttc act gcc     192
Ala Pro Cys Tyr Arg Ser Leu Ser Lys Gly Thr Pro Thr Phe Thr Ala
        50                  55                  60 cac acc cat atg ccc cgc aac tgc tat cac tct gcc act ctt tgc atg     240
His Thr His Met Pro Arg Asn Cys Tyr His Ser Ala Thr Leu Cys Met
65                  70                  75                  80
```

|  |  |
|---|---|
| cat gca aat act cat tat tgg aca gga aaa atg att aat cct agt tgt<br>His Ala Asn Thr His Tyr Trp Thr Gly Lys Met Ile Asn Pro Ser Cys<br>85                           90                      95 | 288 |
| cct gga gga ctt gga gtc act gtc tgt tgg act tac ttc acc caa act<br>Pro Gly Gly Leu Gly Val Thr Val Cys Trp Thr Tyr Phe Thr Gln Thr<br>              100                     105                     110 | 336 |
| ggt atg tct gat ggg ggt gga gtt caa gat cag gca aga gaa aaa cat<br>Gly Met Ser Asp Gly Gly Gly Val Gln Asp Gln Ala Arg Glu Lys His<br>       115                     120                     125 | 384 |
| gta aaa gaa gta atc tcc caa ctc acc cgg gta cat ggc acc tct agc<br>Val Lys Glu Val Ile Ser Gln Leu Thr Arg Val His Gly Thr Ser Ser<br>130                       135                     140 | 432 |
| ccc tac aaa gga cta gat ctc tca aaa cta cat gaa acc ctc cgt acc<br>Pro Tyr Lys Gly Leu Asp Leu Ser Lys Leu His Glu Thr Leu Arg Thr<br>145                   150                     155                     160 | 480 |
| cat act cgc ctg gta agc cta ttt aat acc acc ctc act ggg ctc cat<br>His Thr Arg Leu Val Ser Leu Phe Asn Thr Thr Leu Thr Gly Leu His<br>                  165                   170                     175 | 528 |
| gag gtc tcg gcc caa aac cct act aac tgt tgg ata tgc ctc ccc ctg<br>Glu Val Ser Ala Gln Asn Pro Thr Asn Cys Trp Ile Cys Leu Pro Leu<br>                180                     185                     190 | 576 |
| aac ttc agg cca tat gtt tca atc cct gta cct gaa caa tgg aac aac<br>Asn Phe Arg Pro Tyr Val Ser Ile Pro Val Pro Glu Gln Trp Asn Asn<br>               195                     200                   205 | 624 |
| ttc agc aca gaa ata aac acc act tcc gtt tta gta gga cct ctt gtt<br>Phe Ser Thr Glu Ile Asn Thr Thr Ser Val Leu Val Gly Pro Leu Val<br>       210                     215                     220 | 672 |
| tcc aat ctg gaa ata acc cat acc tca aac ctc acc tgt gta aaa ttt<br>Ser Asn Leu Glu Ile Thr His Thr Ser Asn Leu Thr Cys Val Lys Phe<br>225                     230                     235                     240 | 720 |
| agc aat act aca tac aca acc aac tcc caa tgc atc agg tgg gta act<br>Ser Asn Thr Thr Tyr Thr Thr Asn Ser Gln Cys Ile Arg Trp Val Thr<br>                  245                     250                     255 | 768 |
| cct ccc aca caa ata gtc tgc cta ccc tca gga ata ttt ttt gtc tgt<br>Pro Pro Thr Gln Ile Val Cys Leu Pro Ser Gly Ile Phe Phe Val Cys<br>             260                     265                     270 | 816 |
| ggt acc tca gcc tat cgt tgt ttg aat ggc tct tca gaa tct atg tgc<br>Gly Thr Ser Ala Tyr Arg Cys Leu Asn Gly Ser Ser Glu Ser Met Cys<br>       275                     280                     285 | 864 |
| ttc ctc tca ttc tta gtg ccc cct atg acc atc tac act gaa caa gat<br>Phe Leu Ser Phe Leu Val Pro Pro Met Thr Ile Tyr Thr Glu Gln Asp<br>290                       295                     300 | 912 |
| tta tac agt tat gtc ata tct aag ccc cgc aac aaa aga gta ccc att<br>Leu Tyr Ser Tyr Val Ile Ser Lys Pro Arg Asn Lys Arg Val Pro Ile<br>305                   310                     315                     320 | 960 |
| ctt cct ttt gtt ata gga gca gga gtg cta ggt gca cta ggt act ggc<br>Leu Pro Phe Val Ile Gly Ala Gly Val Leu Gly Ala Leu Gly Thr Gly<br>                  325                     330                     335 | 1008 |
| att ggc ggt atc aca acc tct act cag ttc tac tac aaa cta tct caa<br>Ile Gly Gly Ile Thr Thr Ser Thr Gln Phe Tyr Tyr Lys Leu Ser Gln<br>                    340                     345                     350 | 1056 |
| gaa cta aat ggg gac atg gaa cgg gtc gcc gac tcc ctg gtc acc ttg<br>Glu Leu Asn Gly Asp Met Glu Arg Val Ala Asp Ser Leu Val Thr Leu<br>                    355                     360                     365 | 1104 |
| caa gat caa ctt aac tcc cta gcg aca gta gtc ctt caa aat cga aga<br>Gln Asp Gln Leu Asn Ser Leu Ala Thr Val Val Leu Gln Asn Arg Arg<br>370                     375                     380 | 1152 |
| gct tta gac ttg cta acc gct gaa aga ggg gga acc tgt tta ttt tta<br>Ala Leu Asp Leu Leu Thr Ala Glu Arg Gly Gly Thr Cys Leu Phe Leu<br>385                     390                     395                     400 | 1200 |

-continued

```
ggg gaa gaa tgc tgt tat tat gtt aat caa tcc gga atc gtc act gag     1248
Gly Glu Glu Cys Cys Tyr Tyr Val Asn Gln Ser Gly Ile Val Thr Glu
            405                 410                 415 aaa gtt aaa gaa att cga gat cga ata caa cgt aga gca gag gag ctt     1296
Lys Val Lys Glu Ile Arg Asp Arg Ile Gln Arg Arg Ala Glu Glu Leu
        420                 425                 430 cga aac act gga ccc tgg ggc ctc ctc agc caa tgg atg ccc tgg att     1344
Arg Asn Thr Gly Pro Trp Gly Leu Leu Ser Gln Trp Met Pro Trp Ile
    435                 440                 445 ctc ccc ttc tta gga cct cta gca gct ata ata ttg cta ctc ctc ttt     1392
Leu Pro Phe Leu Gly Pro Leu Ala Ala Ile Ile Leu Leu Leu Leu Phe
450                 455                 460 gga ccc tgt atc ttt aac ctc ctt gtt aac ttt gtc tct tcc aga atc     1440
Gly Pro Cys Ile Phe Asn Leu Leu Val Asn Phe Val Ser Ser Arg Ile
465                 470                 475                 480 gaa gct gta aaa cta caa atg gag ccc aag atg cag tcc aag act aag     1488
Glu Ala Val Lys Leu Gln Met Glu Pro Lys Met Gln Ser Lys Thr Lys
                485                 490                 495 atc tac cgc aga ccc ctg gac cgg aat gct agc cca cga tct gat gtt     1536
Ile Tyr Arg Arg Pro Leu Asp Arg Asn Ala Ser Pro Arg Ser Asp Val
            500                 505                 510 aat gac atc aaa ggc acc cct cct gag gaa atc tca gct gca caa cct     1584
Asn Asp Ile Lys Gly Thr Pro Pro Glu Glu Ile Ser Ala Ala Gln Pro
        515                 520                 525 cta cta cgc ccc aat tca gca gga agc agt tag                         1617
Leu Leu Arg Pro Asn Ser Ala Gly Ser Ser
    530                 535
```

<210> SEQ ID NO 57
<211> LENGTH: 538
<212> TYPE: PRT
<213> ORGANISM: Homo sapiens

<400> SEQUENCE: 57

```
Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
        35                  40                  45

Ala Pro Cys Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
        115                 120                 125

Val Lys Glu Val Ile Ser Gln Leu Thr Arg Val His Gly Thr Ser Ser
    130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
```

```
                    180                 185                 190
Asn Phe Arg Pro Tyr Val Ser Ile Pro Val Pro Glu Gln Trp Asn Asn
            195                 200                 205

Phe Ser Thr Glu Ile Asn Thr Thr Ser Val Leu Val Gly Pro Leu Val
210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Thr Val Val Leu Gln Asn Arg Arg
    370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
    450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Asn Ala Ser Pro Arg Ser Asp Val
            500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
    530                 535

<210> SEQ ID NO 58
<211> LENGTH: 1617
<212> TYPE: DNA
<213> ORGANISM: Homo sapiens
<220> FEATURE:
<221> NAME/KEY: CDS
<222> LOCATION: (1)..(1614)
<223> OTHER INFORMATION:

<400> SEQUENCE: 58
```

-continued

| | | |
|---|---|---|
| atg gcc ctc cct tat cat att ttt ctc ttt act gtt ctt tta ccc tct<br>Met Ala Leu Pro Tyr His Ile Phe Leu Phe Thr Val Leu Leu Pro Ser<br>1               5                   10                  15 | 48 | |
| ttc act ctc act gca ccc cct cca tgc cgc tgt atg acc agt agc tcc<br>Phe Thr Leu Thr Ala Pro Pro Pro Cys Arg Cys Met Thr Ser Ser Ser<br>            20                  25                  30 | 96 | |
| cct tac caa gag ttt cta tgg aga atg cag cgt ccc gga aat att gat<br>Pro Tyr Gln Glu Phe Leu Trp Arg Met Gln Arg Pro Gly Asn Ile Asp<br>        35                  40                  45 | 144 | |
| gcc cca tgc tat agg agt ctt tct aag gga acc ccc acc ttc act gcc<br>Ala Pro Cys Tyr Arg Ser Leu Ser Lys Gly Thr Pro Thr Phe Thr Ala<br>    50                  55                  60 | 192 | |
| cac acc cat atg ccc cgc aac tgc tat cac tct gcc act ctt tgc atg<br>His Thr His Met Pro Arg Asn Cys Tyr His Ser Ala Thr Leu Cys Met<br>65                  70                  75                  80 | 240 | |
| cat gca aat act cat tat tgg aca gga aaa atg att aat cct agt tgt<br>His Ala Asn Thr His Tyr Trp Thr Gly Lys Met Ile Asn Pro Ser Cys<br>                85                  90                  95 | 288 | |
| cct gga gga ctt gga gtc act gtc tgt tgg act tac ttc acc caa act<br>Pro Gly Gly Leu Gly Val Thr Val Cys Trp Thr Tyr Phe Thr Gln Thr<br>            100                 105                 110 | 336 | |
| ggt atg tct gat ggg ggt gga gtt caa gat cag gca aga gaa aaa cat<br>Gly Met Ser Asp Gly Gly Gly Val Gln Asp Gln Ala Arg Glu Lys His<br>        115                 120                 125 | 384 | |
| gta aaa gaa gta atc tcc caa ctc acc cgg gta cat ggc acc tct agc<br>Val Lys Glu Val Ile Ser Gln Leu Thr Arg Val His Gly Thr Ser Ser<br>    130                 135                 140 | 432 | |
| ccc tac aaa gga cta gat ctc tca aaa cta cat gaa acc ctc cgt acc<br>Pro Tyr Lys Gly Leu Asp Leu Ser Lys Leu His Glu Thr Leu Arg Thr<br>145                 150                 155                 160 | 480 | |
| cat act cgc ctg gta agc cta ttt aat acc acc ctc act ggg ctc cat<br>His Thr Arg Leu Val Ser Leu Phe Asn Thr Thr Leu Thr Gly Leu His<br>                165                 170                 175 | 528 | |
| gag gtc tcg gcc caa aac cct act aac tgt tgg ata tgc ctc ccc ctg<br>Glu Val Ser Ala Gln Asn Pro Thr Asn Cys Trp Ile Cys Leu Pro Leu<br>            180                 185                 190 | 576 | |
| aac ttc agg cca tat gtt tca atc cct gta cct gaa caa tgg aac aac<br>Asn Phe Arg Pro Tyr Val Ser Ile Pro Val Pro Glu Gln Trp Asn Asn<br>        195                 200                 205 | 624 | |
| ttc agc aca gaa ata aac acc act tcc gtt tta gta gga cct ctt gct<br>Phe Ser Thr Glu Ile Asn Thr Thr Ser Val Leu Val Gly Pro Leu Ala<br>    210                 215                 220 | 672 | |
| tcc aat ctg gaa ata acc cat acc tca aac ctc acc tgt gta aaa ttt<br>Ser Asn Leu Glu Ile Thr His Thr Ser Asn Leu Thr Cys Val Lys Phe<br>225                 230                 235                 240 | 720 | |
| agc aat act aca tac aca acc aac tcc caa tgc atc agg tgg gta act<br>Ser Asn Thr Thr Tyr Thr Thr Asn Ser Gln Cys Ile Arg Trp Val Thr<br>                245                 250                 255 | 768 | |
| cct ccc aca caa ata gtc tgc cta ccc tca gga ata ttt ttt gtc tgt<br>Pro Pro Thr Gln Ile Val Cys Leu Pro Ser Gly Ile Phe Phe Val Cys<br>            260                 265                 270 | 816 | |
| ggt acc tca gcc tat cgt tgt ttg aat ggc tct tca gaa tct atg tgc<br>Gly Thr Ser Ala Tyr Arg Cys Leu Asn Gly Ser Ser Glu Ser Met Cys<br>        275                 280                 285 | 864 | |
| ttc ctc tca ttc tta gtg ccc cct atg acc atc tac act gaa caa gat<br>Phe Leu Ser Phe Leu Val Pro Pro Met Thr Ile Tyr Thr Glu Gln Asp<br>    290                 295                 300 | 912 | |
| tta tac aat tat gtc ata tct aag ccc cgc aac aaa aga gta ccc att<br>Leu Tyr Asn Tyr Val Ile Ser Lys Pro Arg Asn Lys Arg Val Pro Ile | 960 | |

```
                305                 310                 315                 320
ctt cct ttt gtt ata gga gca gga gtg cta ggt gca cta ggt act ggc          1008
Leu Pro Phe Val Ile Gly Ala Gly Val Leu Gly Ala Leu Gly Thr Gly
                325                 330                 335 att ggc ggt atc aca acc tct act cag ttc tac tac aaa cta tct caa          1056
Ile Gly Gly Ile Thr Thr Ser Thr Gln Phe Tyr Tyr Lys Leu Ser Gln
            340                 345                 350 gaa cta aat ggg gac atg gaa cgg gtc gcc gac tcc ctg gtc acc ttg          1104
Glu Leu Asn Gly Asp Met Glu Arg Val Ala Asp Ser Leu Val Thr Leu
        355                 360                 365 caa gat caa ctt aac tcc cta gcg aca gta gtc ctt caa aat cga aga          1152
Gln Asp Gln Leu Asn Ser Leu Ala Thr Val Val Leu Gln Asn Arg Arg
    370                 375                 380 gct tta gac ttg cta acc gct gaa aga ggg gga acc tgt tta ttt tta          1200
Ala Leu Asp Leu Leu Thr Ala Glu Arg Gly Gly Thr Cys Leu Phe Leu
385                 390                 395                 400 ggg gaa gaa tgc tgt tat tat gtt aat caa tcc gga atc gtc act gag          1248
Gly Glu Glu Cys Cys Tyr Tyr Val Asn Gln Ser Gly Ile Val Thr Glu
                405                 410                 415 aaa gtt aaa gaa att cga gat cga ata caa cgt aga gca gag gag ctt          1296
Lys Val Lys Glu Ile Arg Asp Arg Ile Gln Arg Arg Ala Glu Glu Leu
            420                 425                 430 cga aac act gga ccc tgg ggc ctc ctc agc caa tgg atg ccc tgg att          1344
Arg Asn Thr Gly Pro Trp Gly Leu Leu Ser Gln Trp Met Pro Trp Ile
        435                 440                 445 ctc ccc ttc tta gga cct cta gca gct ata ata ttg cta ctc ctc ttt          1392
Leu Pro Phe Leu Gly Pro Leu Ala Ala Ile Ile Leu Leu Leu Leu Phe
    450                 455                 460 gga ccc tgt atc ttt aac ctc ctt gtt aac ttt gtc tct tcc aga atc          1440
Gly Pro Cys Ile Phe Asn Leu Leu Val Asn Phe Val Ser Ser Arg Ile
465                 470                 475                 480 gaa gct gta aaa cta caa atg gag ccc aag atg cag tcc aag act aag          1488
Glu Ala Val Lys Leu Gln Met Glu Pro Lys Met Gln Ser Lys Thr Lys
                485                 490                 495 atc tac cgc aga ccc ctg gac cgg aat gct agc cca cga tct gat gtt          1536
Ile Tyr Arg Arg Pro Leu Asp Arg Asn Ala Ser Pro Arg Ser Asp Val
            500                 505                 510 aat gac atc aaa ggc acc cct cct gag gaa atc tca gct gca caa cct          1584
Asn Asp Ile Lys Gly Thr Pro Pro Glu Glu Ile Ser Ala Ala Gln Pro
        515                 520                 525 cta cta cgc ccc aat tca gca gga agc agt tag                              1617
Leu Leu Arg Pro Asn Ser Ala Gly Ser Ser
    530                 535

<210> SEQ ID NO 59
<211> LENGTH: 538
<212> TYPE: PRT
<213> ORGANISM: Homo sapiens

<400> SEQUENCE: 59

Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser Ser
                20                  25                  30

Pro Tyr Gln Glu Phe Leu Trp Arg Met Gln Arg Pro Gly Asn Ile Asp
            35                  40                  45

Ala Pro Cys Tyr Arg Ser Leu Ser Lys Gly Thr Pro Thr Phe Thr Ala
        50                  55                  60

His Thr His Met Pro Arg Asn Cys Tyr His Ser Ala Thr Leu Cys Met
```

-continued

```
             65                  70                  75                  80
His Ala Asn Thr His Tyr Trp Thr Gly Lys Met Ile Asn Pro Ser Cys
                 85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
            115                 120                 125

Val Lys Glu Val Ile Ser Gln Leu Thr Arg Val His Gly Thr Ser Ser
        130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
            195                 200                 205

Phe Ser Thr Glu Ile Asn Thr Thr Ser Val Leu Val Gly Pro Leu Ala
        210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
            275                 280                 285

Phe Leu Ser Phe Leu Val Pro Pro Met Thr Ile Tyr Thr Glu Gln Asp
        290                 295                 300

Leu Tyr Asn Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
            355                 360                 365

Gln Asp Gln Leu Asn Ser Leu Ala Thr Val Val Leu Gln Asn Arg Arg
        370                 375                 380

Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Arg Ala Glu Glu Leu
            420                 425                 430

Arg Asn Thr Gly Pro Trp Gly Leu Leu Ser Gln Trp Met Pro Trp Ile
            435                 440                 445

Leu Pro Phe Leu Gly Pro Leu Ala Ala Ile Ile Leu Leu Leu Leu Phe
        450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495
```

Ile Tyr Arg Arg Pro Leu Asp Arg Asn Ala Ser Pro Arg Ser Asp Val
        500                 505                 510

Asn Asp Ile Lys Gly Thr Pro Pro Glu Glu Ile Ser Ala Ala Gln Pro
            515                 520                 525

Leu Leu Arg Pro Asn Ser Ala Gly Ser Ser
    530                 535

<210> SEQ ID NO 60
<211> LENGTH: 1617
<212> TYPE: DNA
<213> ORGANISM: Homo sapiens
<220> FEATURE:
<221> NAME/KEY: CDS
<222> LOCATION: (1)..(1614)
<223> OTHER INFORMATION:

<400> SEQUENCE: 60

| | | |
|---|---|---|
| atg gcc ctc cct tat cat att ttt ctc ttt act gtt ctt tta ccc tct<br>Met Ala Leu Pro Tyr His Ile Phe Leu Phe Thr Val Leu Leu Pro Ser<br>1               5                   10                  15 | 48 |
| ttc act ctc act gca ccc cct cca tgc cgc tgt atg acc agt agc tcc<br>Phe Thr Leu Thr Ala Pro Pro Pro Cys Arg Cys Met Thr Ser Ser Ser<br>            20                  25                  30 | 96 |
| cct tac caa gag ttt cta tgg aga atg cag cgt ccc gga aat att gat<br>Pro Tyr Gln Glu Phe Leu Trp Arg Met Gln Arg Pro Gly Asn Ile Asp<br>        35                  40                  45 | 144 |
| gcc cca tgc tat agg agt ctt tct aag gga acc ccc acc ttc act gcc<br>Ala Pro Cys Tyr Arg Ser Leu Ser Lys Gly Thr Pro Thr Phe Thr Ala<br>    50                  55                  60 | 192 |
| cac acc cat atg ccc cgc aac tgc tat cac tct gcc act ctt tgc atg<br>His Thr His Met Pro Arg Asn Cys Tyr His Ser Ala Thr Leu Cys Met<br>65                  70                  75                  80 | 240 |
| cat gca aat act cat tat tgg aca gga aaa atg att aat cct agt tgt<br>His Ala Asn Thr His Tyr Trp Thr Gly Lys Met Ile Asn Pro Ser Cys<br>                85                  90                  95 | 288 |
| cct gga gga ctt gga gtc act gtc tgt tgg act tac ttc acc caa act<br>Pro Gly Gly Leu Gly Val Thr Val Cys Trp Thr Tyr Phe Thr Gln Thr<br>            100                 105                 110 | 336 |
| ggt atg tct gat ggg ggt gga gtt caa gat cag gca aga gaa aaa cat<br>Gly Met Ser Asp Gly Gly Gly Val Gln Asp Gln Ala Arg Glu Lys His<br>        115                 120                 125 | 384 |
| gca aaa gaa gta atc tcc caa ctc acc cgg gta cat ggc acc tct agc<br>Ala Lys Glu Val Ile Ser Gln Leu Thr Arg Val His Gly Thr Ser Ser<br>    130                 135                 140 | 432 |
| ccc tac aaa gga cta gat ctc tca aaa cta cat gaa acc ctc cgt acc<br>Pro Tyr Lys Gly Leu Asp Leu Ser Lys Leu His Glu Thr Leu Arg Thr<br>145                 150                 155                 160 | 480 |
| cat act cgc ctg gta agc cta ttt aat acc acc ctc act ggg ctc cat<br>His Thr Arg Leu Val Ser Leu Phe Asn Thr Thr Leu Thr Gly Leu His<br>                165                 170                 175 | 528 |
| gag gtc tcg gcc caa aac cct act aac tgt tgg ata tgc ctc ccc ctg<br>Glu Val Ser Ala Gln Asn Pro Thr Asn Cys Trp Ile Cys Leu Pro Leu<br>            180                 185                 190 | 576 |
| aac ttc agg cca tat gtt tca atc cct gta cct gaa caa tgg aac aac<br>Asn Phe Arg Pro Tyr Val Ser Ile Pro Val Pro Glu Gln Trp Asn Asn<br>        195                 200                 205 | 624 |
| ttc agc aca gaa ata aac acc act tcc gtt tta gta gga cct ctt gtt<br>Phe Ser Thr Glu Ile Asn Thr Thr Ser Val Leu Val Gly Pro Leu Val<br>    210                 215                 220 | 672 |
| tcc aat ctg gaa ata acc cat acc tca aac ctc acc tgt gta aaa ttt<br> | 720 |

```
Ser Asn Leu Glu Ile Thr His Thr Ser Asn Leu Thr Cys Val Lys Phe
225                 230                 235                 240 agc aat act aca tac aca acc aac tcc caa tgc atc agg tgg gta act      768
Ser Asn Thr Thr Tyr Thr Thr Asn Ser Gln Cys Ile Arg Trp Val Thr
            245                 250                 255 cct ccc aca caa ata gtc tgc cta ccc tca gga ata ttt ttt gtc tgt      816
Pro Pro Thr Gln Ile Val Cys Leu Pro Ser Gly Ile Phe Phe Val Cys
                260                 265                 270 ggt acc tca gcc tat cgt tgt ttg aat ggc tct tca gaa tct atg tgc      864
Gly Thr Ser Ala Tyr Arg Cys Leu Asn Gly Ser Ser Glu Ser Met Cys
        275                 280                 285 ttc ctc tca ttc tta gtg ccc cct atg acc atc tac act gaa caa gat      912
Phe Leu Ser Phe Leu Val Pro Pro Met Thr Ile Tyr Thr Glu Gln Asp
290                 295                 300 tta tac agt tat gtc ata tct aag ccc cgc aac aaa aga gta ccc att      960
Leu Tyr Ser Tyr Val Ile Ser Lys Pro Arg Asn Lys Arg Val Pro Ile
305                 310                 315                 320 ctt cct ttt gtt ata gga gca gga gtg cta ggt gca cta ggt act ggc     1008
Leu Pro Phe Val Ile Gly Ala Gly Val Leu Gly Ala Leu Gly Thr Gly
                325                 330                 335 att ggc ggt atc aca acc tct act cag ttc tac tac aaa cta tct caa     1056
Ile Gly Gly Ile Thr Thr Ser Thr Gln Phe Tyr Tyr Lys Leu Ser Gln
                340                 345                 350 gaa cta aat ggg gac atg gaa cgg gtc gcc gac tcc ctg gtc acc ttg     1104
Glu Leu Asn Gly Asp Met Glu Arg Val Ala Asp Ser Leu Val Thr Leu
        355                 360                 365 caa gat caa ctt aac tcc cta gcg aca gta gtc ctt caa aat cga aga     1152
Gln Asp Gln Leu Asn Ser Leu Ala Thr Val Val Leu Gln Asn Arg Arg
370                 375                 380 gct tta gac ttg cta acc gct gaa aga ggg gga acc tgt tta ttt tta     1200
Ala Leu Asp Leu Leu Thr Ala Glu Arg Gly Gly Thr Cys Leu Phe Leu
385                 390                 395                 400 ggg gaa gaa tgc tgt tat tat gtt aat caa tcc gga atc gtc act gag     1248
Gly Glu Glu Cys Cys Tyr Tyr Val Asn Gln Ser Gly Ile Val Thr Glu
                405                 410                 415 aaa gtt aaa gaa att cga gat cga ata caa cgt aga gca gag gag ctt     1296
Lys Val Lys Glu Ile Arg Asp Arg Ile Gln Arg Arg Ala Glu Glu Leu
                420                 425                 430 cga aac act gga ccc tgg ggc ctc ctc agc caa tgg atg ccc tgg att     1344
Arg Asn Thr Gly Pro Trp Gly Leu Leu Ser Gln Trp Met Pro Trp Ile
        435                 440                 445 ctc ccc ttc tta gga cct cta gca gct ata ata ttg cta ctc ctc ttt     1392
Leu Pro Phe Leu Gly Pro Leu Ala Ala Ile Ile Leu Leu Leu Leu Phe
450                 455                 460 gga ccc tgt atc ttt aac ctc ctt gtt aac ttt gtc tct tcc aga atc     1440
Gly Pro Cys Ile Phe Asn Leu Leu Val Asn Phe Val Ser Ser Arg Ile
465                 470                 475                 480 gaa gct gta aaa cta caa atg gag ccc aag atg cag tcc aag act aag     1488
Glu Ala Val Lys Leu Gln Met Glu Pro Lys Met Gln Ser Lys Thr Lys
                485                 490                 495 atc tac cgc aga ccc ctg gac cgg aat gct agc cca cga tct gat gtt     1536
Ile Tyr Arg Arg Pro Leu Asp Arg Asn Ala Ser Pro Arg Ser Asp Val
                500                 505                 510 aat gac atc aaa ggc acc cct cct gag gaa atc tca gct gca caa cct     1584
Asn Asp Ile Lys Gly Thr Pro Pro Glu Glu Ile Ser Ala Ala Gln Pro
        515                 520                 525 cta cta cgc ccc aat tca gca gga agc agt tag                         1617
Leu Leu Arg Pro Asn Ser Ala Gly Ser Ser
        530                 535
```

<210> SEQ ID NO 61
<211> LENGTH: 538
<212> TYPE: PRT
<213> ORGANISM: Homo sapiens

<400> SEQUENCE: 61

```
Met Ala Leu Pro Tyr His Ile Phe Leu Phe Thr Val Leu Leu Pro Ser
1               5                   10                  15

Phe Thr Leu Thr Ala Pro Pro Cys Arg Cys Met Thr Ser Ser
            20                  25                  30

Pro Tyr Gln Glu Phe Leu Trp Arg Met Gln Arg Pro Gly Asn Ile Asp
        35                  40                  45

Ala Pro Cys Tyr Arg Ser Leu Ser Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
        115                 120                 125

Ala Lys Glu Val Ile Ser Gln Leu Thr Arg Val His Gly Thr Ser Ser
    130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys Leu Pro Leu
            180                 185                 190

Asn Phe Arg Pro Tyr Val Ser Ile Pro Val Pro Glu Gln Trp Asn Asn
        195                 200                 205

Phe Ser Thr Glu Ile Asn Thr Thr Ser Val Leu Val Gly Pro Leu Val
    210                 215                 220

Ser Asn Leu Glu Ile Thr His Thr Ser Asn Leu Thr Cys Val Lys Phe
225                 230                 235                 240

Ser Asn Thr Thr Tyr Thr Thr Asn Ser Gln Cys Ile Arg Trp Val Thr
                245                 250                 255

Pro Pro Thr Gln Ile Val Cys Leu Pro Ser Gly Ile Phe Phe Val Cys
            260                 265                 270

Gly Thr Ser Ala Tyr Arg Cys Leu Asn Gly Ser Ser Glu Ser Met Cys
        275                 280                 285

Phe Leu Ser Phe Leu Val Pro Pro Met Thr Ile Tyr Thr Glu Gln Asp
    290                 295                 300

Leu Tyr Ser Tyr Val Ile Ser Lys Pro Arg Asn Lys Arg Val Pro Ile
305                 310                 315                 320

Leu Pro Phe Val Ile Gly Ala Gly Val Leu Gly Ala Leu Gly Thr Gly
                325                 330                 335

Ile Gly Gly Ile Thr Thr Ser Thr Gln Phe Tyr Tyr Lys Leu Ser Gln
            340                 345                 350

Glu Leu Asn Gly Asp Met Glu Arg Val Ala Asp Ser Leu Val Thr Leu
        355                 360                 365

Gln Asp Gln Leu Asn Ser Leu Ala Thr Val Val Leu Gln Asn Arg Arg
    370                 375                 380
```

```
Ala Leu Asp Leu Leu Thr Ala Glu Arg Gly Gly Thr Cys Leu Phe Leu
385                 390                 395                 400

Gly Glu Glu Cys Cys Tyr Tyr Val Asn Gln Ser Gly Ile Val Thr Glu
                405                 410                 415

Lys Val Lys Glu Ile Arg Asp Arg Ile Gln Arg Ala Glu Glu Leu
            420                 425                 430

Arg Asn Thr Gly Pro Trp Gly Leu Leu Ser Gln Trp Met Pro Trp Ile
        435                 440                 445

Leu Pro Phe Leu Gly Pro Leu Ala Ala Ile Ile Leu Leu Leu Leu Phe
    450                 455                 460

Gly Pro Cys Ile Phe Asn Leu Leu Val Asn Phe Val Ser Ser Arg Ile
465                 470                 475                 480

Glu Ala Val Lys Leu Gln Met Glu Pro Lys Met Gln Ser Lys Thr Lys
                485                 490                 495

Ile Tyr Arg Arg Pro Leu Asp Arg Asn Ala Ser Pro Arg Ser Asp Val
            500                 505                 510

Asn Asp Ile Lys Gly Thr Pro Pro Glu Glu Ile Ser Ala Ala Gln Pro
        515                 520                 525

Leu Leu Arg Pro Asn Ser Ala Gly Ser Ser
    530                 535

<210> SEQ ID NO 62
<211> LENGTH: 246
<212> TYPE: DNA
<213> ORGANISM: Homo sapiens

<400> SEQUENCE: 62
tgagagacag gactagctgg atttcctagg ccgactaaga atccctaagc ctagctggga      60
argtgaccac gtccaccttt aaacacgggg cttgcaactt agctcacacc tgaccaatca     120
gagagctcac taaaatgcta attaggcaaa gacrggaggt aaagaaatag ccaatcatct     180
attgcctgag agcacagcag gagggacaay ratcgggata taaacccarg ymttcgagcy     240
ggcaac                                                                246

<210> SEQ ID NO 63
<211> LENGTH: 246
<212> TYPE: DNA
<213> ORGANISM: Homo sapiens

<400> SEQUENCE: 63
tgagagacag gactagctgg atttcctagg ccgactaaga atccctaagc ctagctggga      60
aggtgaccac gtccaccttt aaacacgggg cttgcaactt agctcacacc tgaccaatca     120
gagagctcac taaaatgcta attaggcaaa gacaggaggt aaagaaatag ccaatcatct     180
attgcctgag agcacagcag gagggacaat gatcgggata taaacccaag tcttcgagcc     240
ggcaac                                                                246

<210> SEQ ID NO 64
<211> LENGTH: 246
<212> TYPE: DNA
<213> ORGANISM: Homo sapiens

<400> SEQUENCE: 64
tgagagacag gactagctgg atttcctagg ccgactaaga atccctaagc ctagctggga      60
aagtgaccac gtccaccttt aaacacgggg cttgcaactt agctcacacc tgaccaatca     120
```

```
gagagctcac taaaatgcta attaggcaaa gacgggaggt aaagaaatag ccaatcatct       180
attgcctgag agcacagcag gagggacaac aatcgggata taaacccagg cattcgagct       240
ggcaac                                                                  246
```

METHOD FOR DETECTING THE EXPRESSION OF AN ENVELOPE PROTEIN OF A HUMAN ENDOGENOUS RETROVIRUS AND USES OF A GENE CODING FOR SAID PROTEIN

BACKGROUND OF THE INVENTION

1. Field of the Invention

Retroviruses are enveloped viruses which bear glycoprotein spicules encoded by the viruses, at their surface. These envelope glycoproteins are synthesized in the form of polyprotein precursors (Pre-env) which are then cleaved by cellular proteases into mature surface (SU) protein and into transmembrane (TM) protein. Envelope glycoproteins are involved in the entry of viruses into host cells. They specifically recognize and bind to cell surface receptors and are necessary for the fusion of the viral envelope and the cell membranes of the host. The receptor and the envelope are multimeric or oligomeric molecules. For all enveloped viruses, the interactions of the envelope glycoproteins with the cellular receptor(s) lead to conformational rearrangements of the envelope required for exposure of the fusion peptide. The fusion takes place at the surface of the cell or in cellular vesicles, depending on the pathway of endocytosis of the virion. In addition, in order to allow entry of the virus, fusion mediated by the viral surface proteins may, under certain conditions, cause cell-to-cell fusion, resulting in the formation of giant multinucleated cells or syncytia. The formation of syncytia takes place via at least two pathways: a virion may simultaneously fuse with two cells, in which case reference is made to fusion "from without", or an infected cell which expresses the envelope glycoproteins at its surface may fuse with an adjacent cell (fusion "from within").

2. Description of Related Art

The envelope determinants and the sequence of events causing the conformational changes in the envelope during the processes of fusion "from without" are well documented for orthomyxoviruses which require an acid environment in the endocytosis vesicles in order to enter (Skehel, J. J. et al., PNAS, 79:968-972 (1982)). For retroviruses, for which the pathway of entry is independent of the pH, the precise determinants and steps leading from the recognition of the receptor to the activation of the fusion have not yet been elucidated. Other retroviruses are known to induce cell-to-cell fusion ("fusion from within"), such as the feline leukemia virus, the mouse mammary tumor virus, the avian reticuloendotheliosis virus, HIV and SIV.

Moreover, Fefferey S. Jones and Rex Risser (Journal of Virology, January 1993, p. 67-74) have shown that the envelope glycoproteins of the wild-type ecotropic murine leukemia virus (MuLV), under the control of the viral LTR, are capable of inducing the formation of syncytia in rat XC cells in the absence of virions (fusion "from within").

To the inventors' knowledge, the envelope glycoproteins of a human endogenous retrovirus have never been shown to have fusogenic power in a process of fusion "from within".

Some authors have indeed put forward the hypothesis that the endogenous retroviral envelope of ERV3, a human endogenous retrovirus close to MLV (Moloney leukemia virus), may be involved, in vivo, in the development of the placenta via a process of fusion (Patrick J. W. Venables et al., Virology, 211, 589-592 (1995)), but this phenomenon has never been demonstrated in vitro. Furthermore, studies on the polymorphism of ERV3 env on individuals of Caucasian origin, have made it possible to demonstrate the presence of a mutation in the (SU) region of the ERV3 envelope, generating an early stop codon present in the homozygous state in 1% of the population studied, without these individuals exhibiting any abnormality of pregnancy or of placental development (Nathalie de Parseval and Thierry Heidmann, Journal of Virology, Vol. 72, No. 4, pages 3442-3445 (1998)), this casting doubt over the hypothesis previously put forward.

SUMMARY OF THE INVENTION

The present inventors have now demonstrated, in vitro, that the unmodified HERV-W envelope glycoprotein, expressed under the control of a promoter, preferably a heterologous promoter, has fusogenic properties.

HERV-W is a recently described multicopy family of human endogenous retroviruses, so named because of the homology between the attachment site for the reverse transcription primer and that of avian retroviruses which use the Trp tRNA. No competent entity for its replication has been demonstrated. The functionality of a promoter region has been verified and, among various healthy human tissues tested, its expression appears, by Northern blot, to be restricted to the placenta (J. L. Blond et al., Journal of Virology, Vol. 73, No. 2, pages 1175-1185 (1999)). A single open reading frame coding for a potentially functional retroviral envelope exists on chromosome 7. A cDNA clone probably corresponding to a subgenomic transcript and bearing the complete sequence of the envelope has been isolated from placental material (clone cl.PH74, GenBank AF072506, the sequence of which is identified by SEQ ID No. 2). The phylogenetic studies carried out at the protein level indicate that the envelope protein is type D. The sequence SEQ ID No. 2 given at the end of the description therefore corresponds to the complete cDNA nucleotide sequence of the clone cl.PH74, the protein sequence of which is identified by SEQ ID No. 1.

Env HERV-W has all the "attributes" of a retroviral envelope: in particular, a leader peptide and the two characteristic subunits SU and TM separated by a furin cleavage site and, in its TM, it has a hydrophobic fusion peptide, an immunosuppressive region and a transmembrane carboxyl region followed by a long cytoplasmic tail. Env HERV-W expression has been demonstrated in the placenta.

The experiments carried out by the inventors show that Env HERV-W causes, by cell-to-cell fusion, the formation of syncytia in various cell lines tested, of human and simian origin. The fusion phenomenon observed is dependent on the recognition of specific receptor(s), as shown directly in transfections and indirectly in cocultures of transfected cells with other cell types. The present inventors have, moreover, identified the specific receptor for Env HERV-W using a competition approach based on the property of interference of retroviral envelopes, by blocking cellular receptors with an envelope protein other than Env HERV-W, thus preventing the formation of syncytia. The receptor identified by the present inventors is the hATB° receptor for type D mammalian retroviruses, which is expressed in human cells (Rasko E. J. et al. PNAS, 1999, 96: 2129-2134 and Tailor C. S. et al. J. Virol., 1999, 73(5): 4470-4474). The use of this receptor, the method for the demonstration of which is described in one of the examples, is also part of the present invention.

Thus, a subject of the present invention is a method for detecting the expression of an envelope protein or polypeptide of a human endogenous retrovirus, according to which the protein or polypeptide has a polypeptide sequence which comprises the sequence SEQ ID No. 1 or a fragment of SEQ ID No. 1, or a sequence which exhibits, for any series of 20 amino acids, at least 80%, preferably at least 90%, or even at least 95% identity with the sequence SEQ ID No. 1 or with a fragment of SEQ ID No. 1, and according to which the fusogenic power of said protein or of said fragment in cells of a cellular tissue or of a cell culture is detected by demonstrating the formation of syncytia.

Another subject of the invention is a method for detecting the expression of an envelope protein or polypeptide of a human endogenous retrovirus, according to which the protein or polypeptide has a polypeptide sequence which exhibits, for any series of 20 amino acids, at least 80%, preferably at least 90%, or even at least 95% identity with the sequence SEQ ID No. 1, and according to which the fusogenic power of said protein in cells of a cellular tissue or of a cell culture is detected by demonstrating the formation of syncytia.

BRIEF DESCRIPTION OF THE DRAWINGS

Various embodiments will be described in detail, with reference to the following figures, wherein:

FIG. 1 illustrates examples of polymorphic HERV-W envelope amino acid sequences;

FIGS. 2A-2B illustrate examples of polymorphic HERV-W envelope nucleic acid sequences;

FIG. 5 is a schematic representation of cell-cell fusion tests involving HERV-W Env chimeras.

DETAILED DESCRIPTION OF EMBODIMENTS

According to the invention, said protein or said polypeptide has a polypeptide sequence which comprises the sequence SEQ ID No. 1 or a fragment of SEQ ID No. 1, or a sequence which exhibits, for any series of 20 amino acids, at least 80%, preferably at least 90%, or even at least 95% identity with the sequence SEQ ID No. 1 or with a fragment of SEQ ID No. 1.

According to the present invention, it is clearly understood that said protein or said polypeptide, or said fragments thereof, if they do not exhibit complete identity with SEQ ID No. 1 or its fragments, should have a fusogenic power preferably at least equal to or greater than that of SEQ ID No. 1 or its fragments.

If the fragments of the protein or of the polypeptide of the invention exhibit complete identity with the fragments of SEQ ID No. 1, then the size of these fragments may be less than 20 amino acids, for example it may be approximately 10 amino acids, or even approximately 5 amino acids.

The variations envisaged according to the invention in the polypeptide sequence of the protein or of the polypeptide, or of their fragments, comprise the variations linked to the polymorphism, but also modifications such as substitution(s), deletion(s) and addition(s) which may be introduced into said polypeptide sequence in order to obtain a protein, a polypeptide, or a fragment thereof, which has fusogenic power, in particular at least equal to or greater than that of SEQ ID No. 1 or its fragments.

Figure 4:
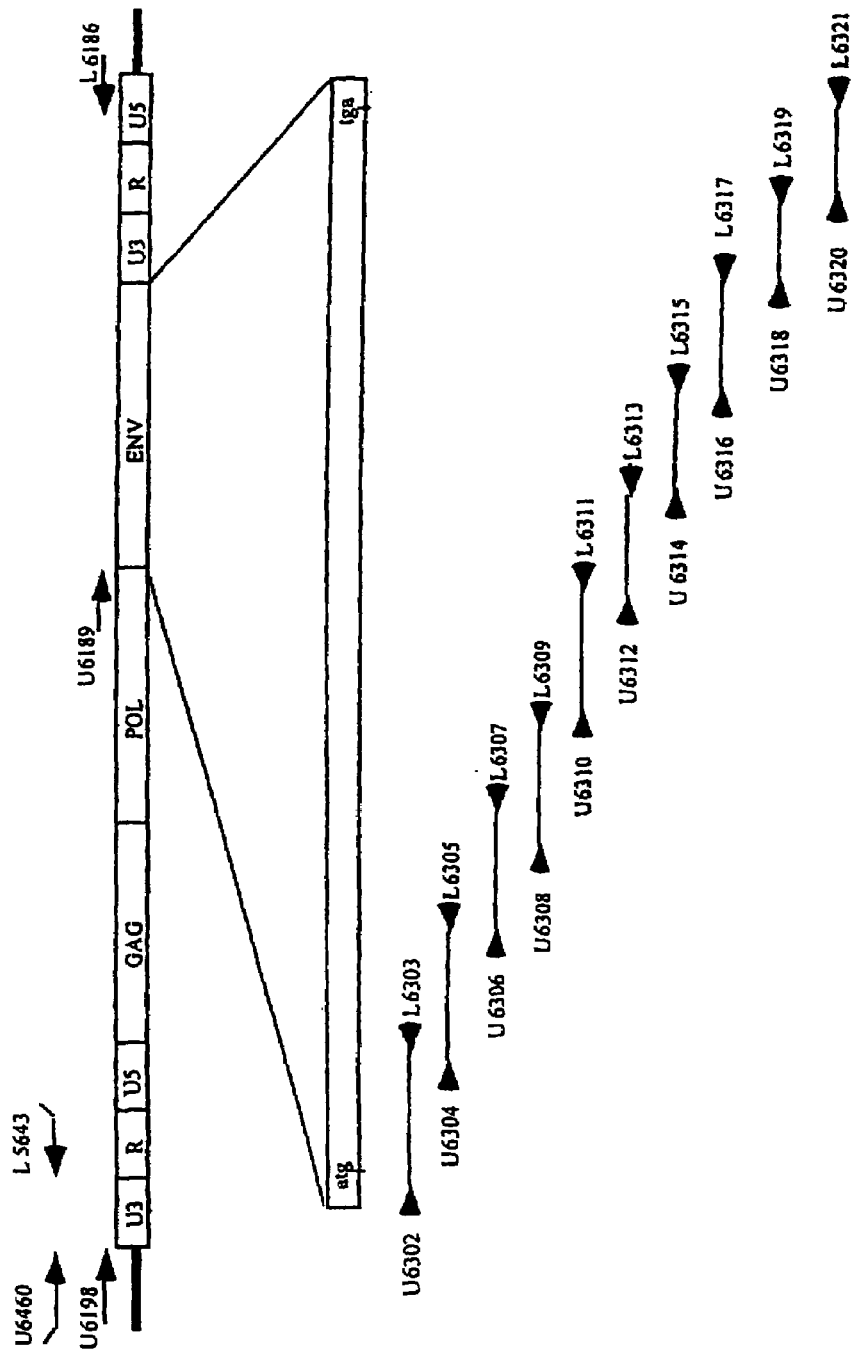
FIG. 4 is a schematic representation of a polymorphism analysis of the HERV-W envelope gene.

The polymorphism analysis may be carried out by the SSCP (single strand conformational polymorphism) method, which is an electrophoretic method which makes it possible to objectify, using differences in migration, the presence of at least one mutation which distinguishes two short sequences (less than 250 bp). Thus, as illustrated in FIG. 4, after amplification on total DNA using the primers U6198 and L6186, or U6189 and L6186, it is possible to analyze the polymorphism of the envelope located on chromosome 7 using the set of primers represented (U6302 to L6321), making it possible to generate a set of 10 overlapping fragments of suitable size. The polymorphism of one of the subfragments may also be demonstrated by sequencing, mapping and/or restriction techniques, as appropriate, or more simply by a sandwich hybridization technique of the ELOSA type which makes it possible to distinguish as little as a point mutation (Cros P. et al., European patent application EP 0 486 661).

Figure 1:
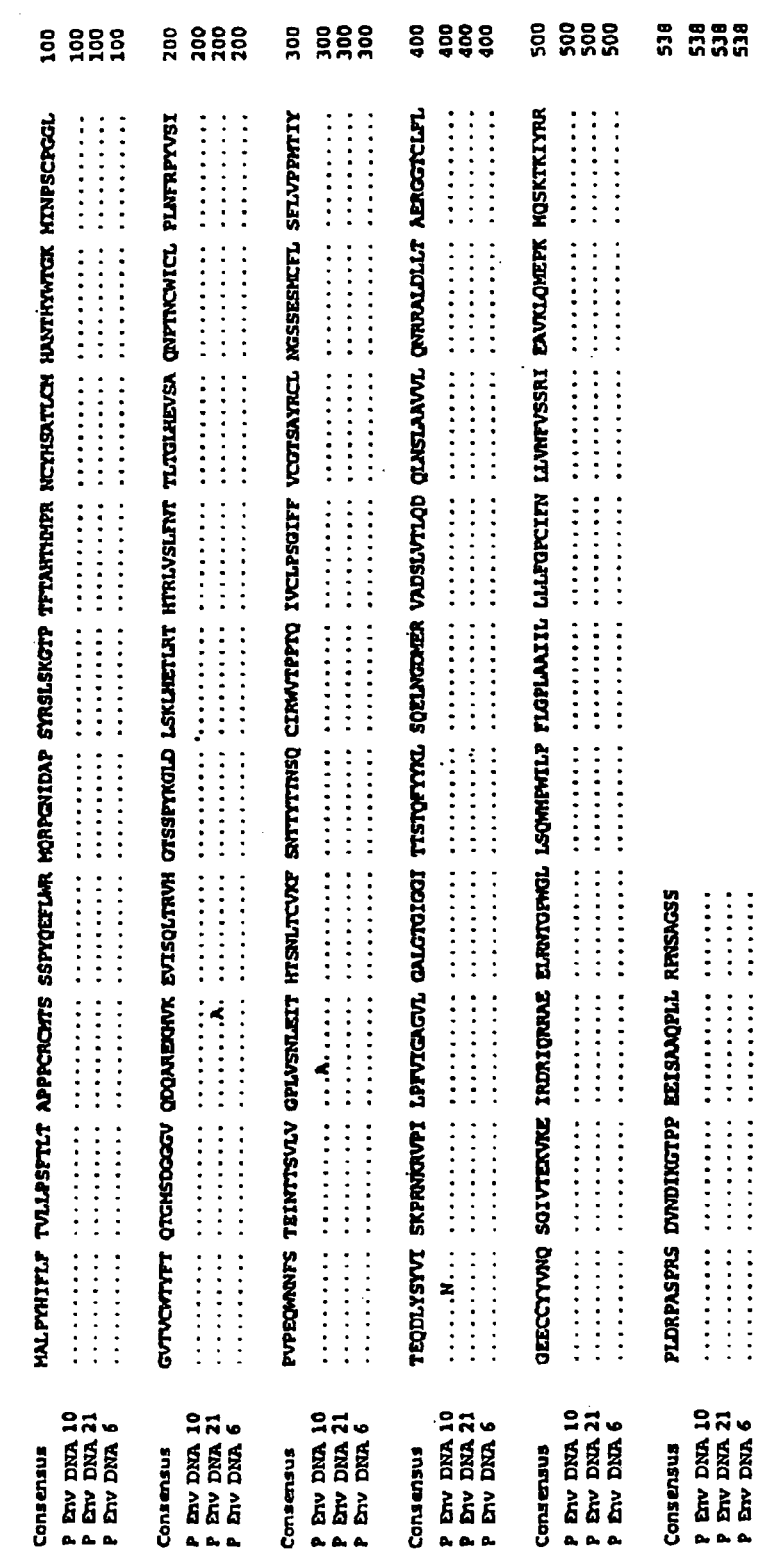
Figure 2A:
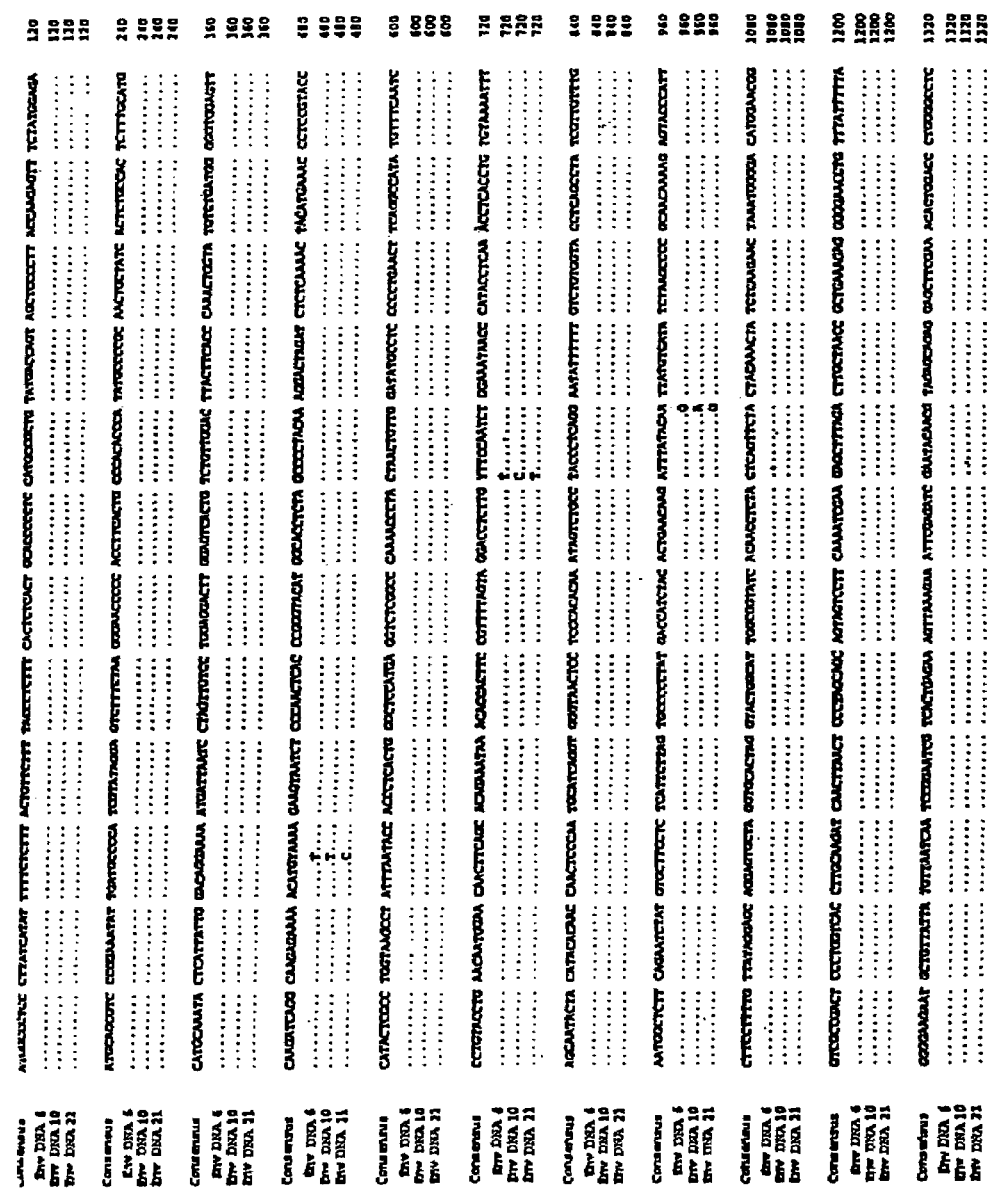
Figure 2B:
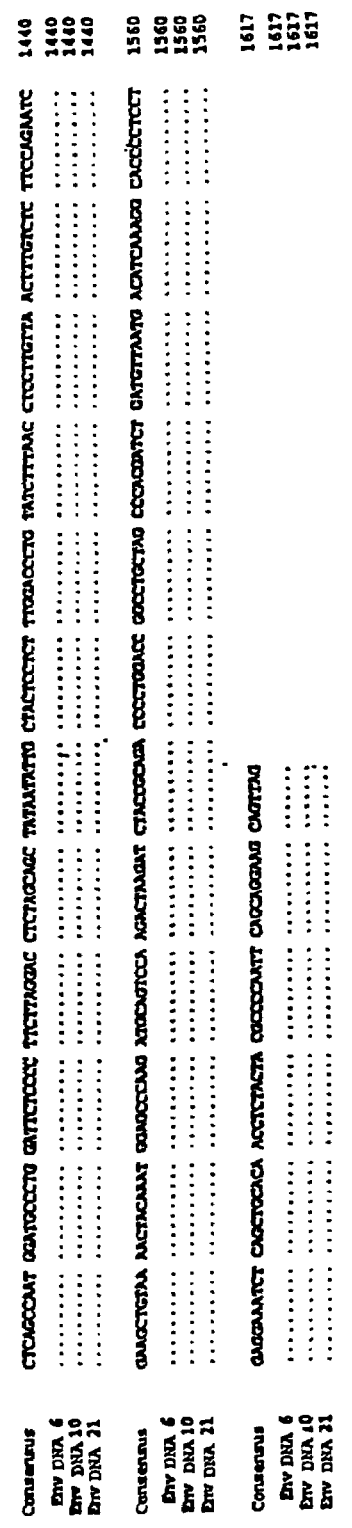

Examples of polymorphic Env HERV-W sequences are represented in the attached FIG. 1, the corresponding DNA sequences being represented in FIG. 2. These figures represent the alignment of protein and nucleic acid sequences obtained by sequencing clones derived from three different individuals. Specifically, FIG. 1 represents the consensus protein sequence (SEQ ID NO:55) aligned with the three individual protein sequences respectively labeled DNA 6 (SEQ ID NO:57), DNA 10 (SEQ ID NO:59) and DNA 21 (SEQ ID NO:61), and FIG. 2 represents the corresponding consensus DNA sequence (SEQ ID NO:54) aligned with the three individual DNA sequences respectively labeled DNA 6 (SEQ ID NO:56), DNA 10 (SEQ ID NO:58) and DNA 21 (SEQ ID NO:60).

Figure 3:
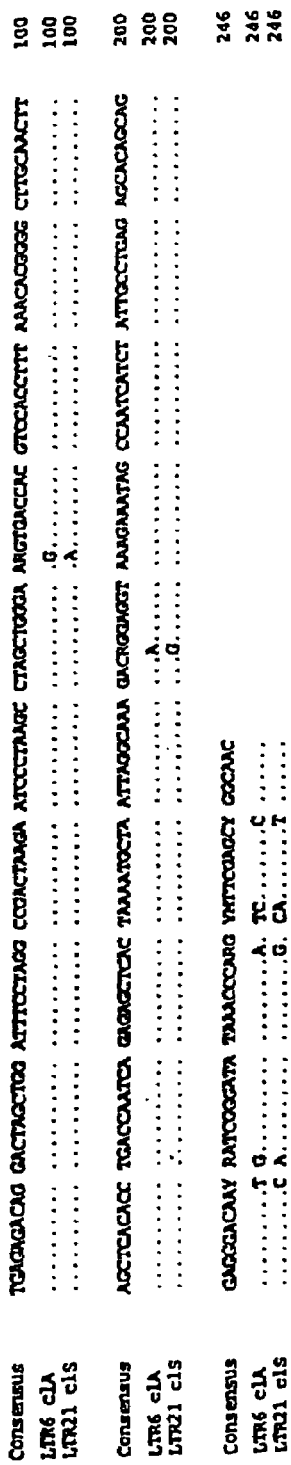
FIG. 3 illustrates examples of polymorphic HERV-W LTR nucleic acid sequences.

Moreover, the polymorphism of the LTR which directs the transcription of the env gene located on chromosome 7 was studied. Two groups of 5' LTRs are observed, the nucleic acid sequences of which, obtained by sequencing two clones originating from two different individuals, are represented and aligned in FIG. 3. Specifically, FIG. 3 represents the consensus DNA sequence (SEQ ID NO:62) aligned with the two individual DNA sequences respectively labeled LTR6 c1A (SEQ ID NO:63) and LTR21 c1S (SEQ ID NO:64).

A judicious choice of primers has made it possible to specifically amplify, on chromosome 7, from total human DNA, a nucleic acid fragment containing all the information U3RU5-gag-pol-env-U3RU5, using the U6198 and L6186 primers, or exclusively the env-U3RU5 sequence, using the U6189 and L6186 primers. Such an approach is, for example, possible using a primer which overlaps the zone where the retrovirus sequence (U3 upstream, U5 downstream) joins the contiguous nonretroviral flanking sequence. For example, the L6186 primer overlaps the terminal 3' U5 region and the downstream nonretroviral sequence. Using such a PCR product isolating the sequence of interest from the mixture of HERV-W sequences present in the human genome, it is possible to carry out an analysis of the polymorphism.

Preferentially, said protein has at least one of the following characteristics:

it is encoded by the env gene of the HERV-W endogenous retrovirus;

it is encoded by an open reading frame located on chromosome 7 of the human genome;

it has a polypeptide sequence which comprises the sequence SEQ ID No. 1, or a sequence which exhibits, for any series of 20 amino acids, at least 80%, preferably at least 90%, or even at least 95% identity with SEQ ID No. 1. Preferably, it consists of SEQ ID No. 1.

Preferentially, the polypeptide has a polypeptide sequence which begins at amino acid 448 and ends at amino acid 538 of SEQ ID No. 1 or a polypeptide sequence which exhibits, for any series of 20 amino acids, at least 80%, preferably at least 90%, or even at least 95% identity with the polypeptide sequence which begins at amino acid 448 and ends at amino acid 538 of SEQ ID No. 1. Preferably, it consists of a polypeptide sequence which begins at amino acid 448 and ends at amino acid 538 of SEQ ID No. 1. The polypeptide which corresponds to the above definition is a regulatory element which can confer or restore its fusogenic capacity on or to a retroviral envelope not reputed to be fusogenic in a cell-cell fusion test.

The cells of said tissue or of said cell culture, in which demonstration of the fusogenic power is sought, are advantageously chosen from bone cells, muscle cells, placenta cells, endothelial cells, in particular of blood vessels, epithelial cells, glial cells and tumor cells or cells derived from tumor cell lines.

As will be illustrated in the following examples, the detection of the fusogenic power of said protein or of said polypeptide may be carried out according to at least any one of the following two protocols.

According to a first protocol, a vector for expression of said protein or of said polypeptide is obtained, based on which the expression of the protein, of the polypeptide or of its gene is under the control of a promoter, preferably a strong promoter; cells are transfected with the vector obtained, so as to obtain producer cells expressing, at their surface, said protein or said polypeptide; and the formation of syncytia or the absence of formation of syncytia is observed.

According to a second protocol, a vector for expression of said protein or said polypeptide is obtained, based on which the expression of the protein, of the polypeptide or of its gene is under the control of a promoter, preferably a strong promoter; cells are transfected with the vector obtained, so as to obtain producer cells expressing, at their surface, said protein or said polypeptide; naive indicator cells expressing, at their surface, a receptor for said protein are cocultured in the presence of said producer cells; and the formation of syncytia or the absence of formation of syncytia is observed.

The present invention also relates to the use of a gene or of a nucleic acid, or of a fragment of gene or of a nucleic acid, coding for a protein or a polypeptide as defined above in the description of the methods which are subjects of the invention, under suitable conditions which allow its expression, for preparing a therapeutic or prophylactic composition.

Another subject of the invention is a therapeutic or prophylactic composition comprising a gene or a nucleic acid, or a fragment of gene or of nucleic acid, coding for a protein or a polypeptide as defined above.

Such a composition may also comprise a heterologous or autologous promoter, preferably a heterologous promoter, for the expression of said protein or of said polypeptide.

The invention also relates to the following subjects:
  an expression vector comprising at least one gene or one nucleic acid, or one fragment of gene or of nucleic acid, coding for a protein or a polypeptide as defined above, and elements required for its expression in a host cell;
  a host cell comprising at least one expression vector of the invention, and
  a therapeutic or prophylactic composition comprising at least one expression vector or one host cell of the invention.

The various therapeutic compositions of the invention are in particular intended for the treatment of cancers, such as by destroying the cancer cells by means of the formation of syncytia. The various prophylactic compositions of the invention are in particular intended to prevent a deficiency in placental development.

The therapeutic or prophylactic compositions of the invention, as defined above, are advantageously intended for a treatment commonly named "treatment by gene therapy" or "treatment by gene transfer".

As stated above, the fusogenic properties of the Env HERV-W protein, of the Env HERV-W polypeptide or of their fragments as defined in the present invention in particular find an application in the domain of cancer gene therapy.

To date, the genes most commonly used in therapy against cancers are (i) the genes which code for proteins which increase the immunogenicity of the tumor cells, such as pro-inflammatory cytokines, (ii) the genes which code for enzymes which make the cancer cells sensitive to a promedicament in gene/prodrug systems, such as the Herpes Simplex virus thymidine kinase/Ganciclovir system or the cytosine deaminase/5FC system.

Ideally, the transfer of therapeutic genes should lead both to a local destruction of the cancer cells and to activation of antitumor immunity in order to eliminate the tumor regions to which the therapeutic genes cannot be delivered, and the treatment should not cause damage to the host's normal cellular tissues, in particular to the tissues of the vital organs.

The protein or polypeptide of the invention, which comprises or consists of the Env HERV-W protein or its fragments, in particular a fragment which begins at amino acid 448 and ends at amino acid 538 of SEQ ID No. 1, or of a polypeptide sequence which has, for any series of 20 amino acids, at least 80%, preferably at least 90%, or even at least 95% identity with SEQ ID No. 1 or a fragment of SEQ ID No. 1, and in particular the fragment identified above, under the control of a heterologous or autologous promoter capable of inducing its expression, corresponds to the criteria defined above by the formation of syncytia. The syncytia form from one or more transfected cell(s) by a process of cell-to-cell fusion.

In an embodiment with a view to optimizing its therapeutic characteristics, the protein or polypeptide of the invention, or any fragment, is optionally fused with one or more other protein(s) or protein fragment(s), even if intrinsically it corresponds to the criteria defined above. On the other hand, all or part of the protein, and in particular the polypeptide the peptide sequence of which comprises or consists of the sequence which begins at amino acid 448 and ends at amino acid 538 of SEQ ID No. 1, may be fused with other proteins with a view to conferring on them particular properties. The protein or polypeptide of the invention, or its fragment, is capable of inducing the formation of syncytia at a pH close to neutral or at neutral pH. Typically, the expression vector or plasmid will be adjusted to allow expression of the protein, the polypeptide or the fragment which induces the formation of syncytia, such that, when it is expressed, the protein, polypeptide or fragment may induce the fusion of transfected cells with other nontransfected human cells. It is desirable for the protein or polypeptide of the invention to be expressed independently of other viral components, unless these components are useful for the vectorization.

Thus, a subject of the present invention is a gene or a nucleic acid, or a fragment of gene or of a nucleic acid, which is recombinant and which codes for a protein, a polypeptide or a fragment of the invention which induces the formation of syncytia by fusion of transformed cells and target malignant cells, and its use in the domain of therapy for malignant diseases, such as cancers.

The invention also relates to a method for treating a malignant disease in a patient, which consists in administering to the patient the gene or a nucleic acid, or a fragment of gene or of a nucleic acid, which is recombinant and which codes for a protein, a polypeptide or a fragment of the invention which induces the formation of syncytia by fusion of transformed cells and target malignant cells.

The gene or the nucleic acid, or the fragment of gene or of nucleic acid, is introduced in vitro into suitable human cells, such as cells of immortalized continuous lines, by standard techniques known to those skilled in the art, such as transfection, transduction or transformation, and the cells thus transformed are then introduced into the patient, where they may exert their fusogenic properties.

The gene or the nucleic acid, or the fragment of gene or of nucleic acid, of the invention may be used in various ways for the treatment of cancers, in particular for the treatment of solid or soft tumors. The target cells may be transformed ex vivo or in vivo with the vectors (plasmids) coding for the polypeptide of the invention.

The fusogenic properties of the Env HERV-W protein, of the Env HERV-W polypeptide or of their fragments as defined in the present invention also find an application in the domain of prophylaxis, for preventing a deficiency in placental development and overcoming failed pregnancies.

The gene or the nucleic acid or their fragments as defined in the invention may therefore be used for various therapeutic or prophylactic effects, the ultimate aim being (i) to destroy the target cells by formation of syncytia inducing cell death in the target cells by a process of death other than cell death by apoptosis, or (ii) to induce or to promote the formation of syncytia, for example to overcome a deficiency in the formation of syncytiotrophoblasts during pregnancy, or to prevent a deficiency in the natural formation of any other type of syncytia, said deficiency being associated with a pathology.

The invention also relates to the use of the Env HERV-W protein, or of a fragment of Env HERV-W, as defined above, at the surface of a gene therapy vector comprising, inter alia, a gene, a nucleic acid sequence or an oligonucleotide of therapeutic interest capable of being expressed in a target cell or of hybridizing to a complementary nucleotide sequence from a target cell, said Env HERV-W protein or said fragment of this protein interacting with its cellular receptor described above, thus promoting the introduction of the gene, the nucleic acid sequence or the oligonucleotide of therapeutic interest into the target cell.

Thus, the invention relates to a gene therapy vector comprising an envelope protein, polypeptide or fragment of a human endogenous retrovirus, said protein or said polypeptide having a polypeptide sequence which comprises the sequence SEQ ID No. 1 or a fragment of SEQ ID No. 1, in particular a fragment the peptide sequence of which comprises or consists of the sequence which begins at amino acid 448 and ends at amino acid 538 of SEQ ID No. 1, or a sequence which exhibits, for any series of 20 amino acids, at least 80%, preferably at least 90%, or even at least 95% identity with the sequence SEQ ID No. 1 or with a fragment of SEQ ID No. 1, in particular as defined above. Preferably, the gene therapy vector of the invention comprises the sequence SEQ ID No. 1. In a particular embodiment of the invention, the gene therapy vector mentioned above consists of a conventional retroviral vector of the MLV type or of a lentiviral vector pseudotype with all or part of the envelope protein of HERV-W as defined above, or alternatively of a synthetic vector carrying, at its surface, all or part of the Env HERV-W protein as defined above which confers the properties of cell targeting and of plasma membrane fusion.

The invention also relates to a gene therapy vector comprising, at its surface, the receptor for the protein identified in SEQ ID No. 1, in particular for targeting cells producing the protein identified in SEQ ID No. 1 in a constitutive or induced manner.

The nucleic acid sequences and/or oligonucleotides of therapeutic interest (antisense or coding for a protein) in particular make it possible to target the cells in which a gene is expressed.

The antisense nucleic acid sequences or oligonucleotides are capable of interfering specifically with the synthesis of a target protein, by inhibiting the formation and/or the functioning of the polysome, depending on the position of the antisense in the mRNA of the target. Therefore, the common choice of the sequence surrounding the translation initiation codon as a target for inhibition by an antisense nucleic acid sequence or by an antisense oligonucleotide is aimed at preventing the formation of the initiation complex. Other mechanisms in the inhibition by antisense oligonucleotides involve activation of ribonuclease H, which digests the antisense oligonucleotide/mRNA hybrids, or interference at splicing sites by antisense oligonucleotides whose target is an mRNA splicing site. The antisense oligonucleotides are also complementary to DNA sequences and may therefore interfere at the level of transcription, by forming a triple helix, the antisense oligonucleotide pairing via "Hoogsteen" hydrogen bonds at the level of the major groove of the DNA double helix. In this particular case, reference is made more precisely to anti-gene oligonucleotides. It is clearly understood that the antisense nucleic acid sequences or oligonucleotides may be strictly complementary to the DNA or RNA target to which they must hybridize, but also not strictly complementary, on the condition that they hybridize on the target. Similarly, they may be antisense oligonucleotides which may or may not be modified at the level of the internucleotide bonds. All these notions are part of the general knowledge of those skilled in the art.

The present invention therefore relates to a therapeutic composition comprising, inter alia, a gene therapy vector, the Env HERV-W protein or a fragment of this protein as defined above, and an antisense nucleic acid sequence or oligonucleotide as defined above.

The Env HERV-W protein or one of its fragments is also used as a therapeutic vector for the transfer of a gene of therapeutic interest into a target cell and in the formulation of a therapeutic composition comprising at least one gene therapy vector, the Env HERV-W protein or a fragment of this protein as defined above, and a gene of therapeutic interest, and also the elements which allow the expression of said gene of therapeutic interest. The genes of therapeutic interest may be nonmutated or mutated. They may also consist of nucleic acids modified such that it is impossible for them to integrate into the genome of the target cell, or nucleic acids stabilized with agents, such as spermine.

The expression "elements which ensure the expression of said gene of therapeutic interest in vivo" refers in particular to the elements required to ensure the expression of said therapeutic gene after it has been transferred into a target cell. They are, in particular, promoter sequences and/or regulatory sequences which are effective in said cell and, optionally, the sequences required to allow the expression of a polypeptide at the surface of the target cells. The promoter used may be a viral, ubiquitous or tissue-specific promoter or a synthetic promoter.

By way of example, mention will be made of promoters such as the RSV (Rous Sarcoma Virus), MPSV, SV40 (Simian Virus), CMV (Cytomegalovirus) or vaccinia virus promoters. It is also possible to choose a promoter sequence specific for a given cell type or activatable under defined conditions. The literature provides a great deal of information relating to such promoter sequences.

In another embodiment, use may be made, in a therapeutic composition, of a cell expressing the Env HERV-W protein or a fragment of this protein as defined above, as a vehicle for one or more gene(s) which is large in size, due to the fusogenic properties of the protein or of its fragments, which allow the vector cell to fuse with a host cell deficient for one or more given genes, thus making it possible to compensate for the deficient gene(s) (example: distrophin).

The invention therefore also relates to such a cell and its use as a cellular vector.

The fusogenic properties or power of the protein or of the polypeptide of the invention, or of their fragments, are also used in a method for testing the effectiveness of and selecting medicinal substances or drugs, or gene/prodrug systems, capable of having a qualitative and/or quantitative effect on their fusogenic power, by bringing said medicinal substance or drug, or said gene/prodrug system, into contact with cells of a cell culture expressing said protein or said polypeptide or said fragment, and observing a regression in or a disappearance of the formation of syncytia, it being understood that the formation of syncytia in the natural state is associated with a pathological condition. By way of example, mention may be made of hemorrhagic phenomena, the destruction or modification of neuronal cells, and the exacerbated modification or destruction of osteoblasts.

The invention also relates to a method for selecting medicinal substances or drugs, or gene/prodrug systems, capable of having a qualitative and/or quantitative effect on the fusogenic power of a protein or of a polypeptide or of a fragment as defined above. According to this method, said medicinal substance or drug, or said gene/prodrug system, is brought into contact with cells of a cell culture expressing said protein or said polypeptide or said fragment, and a regression in or a disappearance of the formation of syncytia is observed.

The invention also relates to the use of at least one antisense nucleic acid sequence or of at least one antisense oligonucleotide corresponding to the criteria described above and capable of hybridizing and of interfering specifically with the synthesis of the Env HERV-W protein, and to a therapeutic composition comprising, inter alia, said antisense nucleic acid sequence or oligonucleotide, with the aim of obtaining, in vivo, a regression or a disappearance of syncytia associated with a pathological condition.

With the aim of obtaining, in vivo, regression of the formation of syncytia or disappearance of syncytia associated with a pathological condition, a therapeutic composition is prepared which comprises, inter alia, a ligand capable of recognizing the receptor identified above and of inactivating or inhibiting the process of formation of syncytia, or a composition is prepared which comprises a gene coding for a ligand capable of being expressed, in vivo, in a target cell or in a given target cell tissue, said gene being under the control of the required elements which ensure its expression after it has been transferred into the target cell or cellular tissue.

Thus, the term "ligand" is intended to mean any molecule which is capable of recognizing said receptor and/or of inhibiting its function. It may be, inter alia, a monoclonal antibody or a polyclonal antibody, or a monoclonal antibody or polyclonal antibody fragment. It may also be a molecule which inhibits the function of the receptor, the affinity constant of which would be greater than that of the Env HERV-W protein for its binding and attachment to the receptor.

The production of polyclonal and monoclonal antibodies is part of the general knowledge of those skilled in the art. Mention may be made, by way of reference, of Köhler G. and Milstein C. (1975): Continuous culture of fused cells secreting antibody of predefined specificity, Nature 256: 495-497 and Galfre G. et al. (1977) Nature, 266: 550-552, for the production of monoclonal antibodies, and Roda A., Bolelli G. F.: Production of high-titer antibody to bile acids, Journal of Steroid Biochemistry, Vol. 13, pp 449-454 (1980), for the production of polyclonal antibodies. For the production of monoclonal antibodies, an immunogen may be coupled to Keyhole Limpet Hemocyanin (KLH peptide) as a support for the immunization, or to serum albumin (SA peptide). The animals are given an injection of immunogen using complete Freund's adjuvant. The sera and the hybridoma culture supernatants derived from the immunized animals are analyzed for their specificity and their selectivity, using conventional techniques, such as for example ELISA or Western blot assays. The hybridomas producing the most specific and the most sensitive antibodies are selected. Monoclonal antibodies may also be produced in vitro by cell culture of the hybridomas produced or by recovery of ascites fluid, after intraperitoneal injection of the hybridomas into mice. Whatever the method of production, by supernatant or by ascites, the antibodies are then purified. The purification methods used are essentially ion-exchange gel filtration and exclusion chromatography or immunoprecipitation. A number of antibodies sufficient to identify the most effective ones are screened in functional assays. The in vitro production of antibodies, of antibody fragments or of antibody derivatives, such as chimeric antibodies produced by genetic engineering, is well known to those skilled in the art.

More particularly, the term "antibody fragment" is intended to mean the F(ab)2, Fab, Fab' or sFv fragments (Blazar et al., 1997, Journal of Immunology 159: 5821-5833 and Bird et al., 1988, Science 242: 423-426) of a native antibody, and the term "derivative" is intended, inter alia, to mean a chimeric derivative of a native antibody (see for example Arakawa et al., 1996, J. Biochem 120: 657-662 and Chaudray et al., 1989, Nature 339: 394-397).

As mentioned above, gene therapy opens up the possibility of expressing such ligands in vivo, by administering therapeutic compositions comprising at least one gene coding for such a ligand. Such a gene of therapeutic interest codes, in particular, (i) either for at least one polyclonal or monoclonal antibody, or a monoclonal or polyclonal antibody fragment, or for a native transmembrane antibody, or a fragment of such an antibody, provided that the antibody or antibody fragment is expressed in vivo at the surface of a target cell or of target cells of a tissue and is capable of recognizing and of binding to said receptor, (ii) or for at least one inhibitory molecule as described above.

The expression "target cells" or "target cells of a tissue", as defined above, is intended to mean (i) either cells at the level of which the intention is to act so as to prevent or inhibit the formation of syncytia, (ii) or cells other than these but which are capable of expressing the ligand and, consequently, of inhibiting and/or blocking the functional activity of the receptor.

The expression "element which ensures the expression in vivo of said gene" refers in particular to the elements required to ensure its expression after it has been transferred into a target cell. They are, in particular, the promoter sequences and/or the regulatory sequences which are effective in said cell and, optionally, the sequences required to allow the expression, at their surface, of an inhibitory polypeptide or molecule, as mentioned above. The promoter used may be a viral, ubiquitous or tissue-specific promoter or a synthetic promoter. Examples of such promoters have been described previously.

The term "transmembrane antibody" is intended to mean an antibody in which at least the functional region capable of recognizing and of attaching to the receptor is expressed at the surface of the target cells so as to allow recognition and attachment. Such antibodies may consist of fusion polypeptides comprising an amino acid sequence defining the functional region and an amino acid sequence defining a transmembrane polypeptide which allows the anchoring within the lipid bilayer of the membrane of the target cells or to the external surface of this lipid bilayer. Nucleic acid sequences coding for such transmembrane antibodies are described in the literature.

The expression "gene or nucleic acid sequence or their fragments" is intended to mean (i) an isolated native gene or nucleic acid or their isolated fragments obtained by enzymatic cleavage, or (ii) a gene or nucleic acid or their fragments obtained by chemical synthesis using automatic synthesizers, such as the synthesizers marketed by Applied Biosystems.

The term "tumor cells" is intended to mean (i) cells of immortalized cell lines or (ii) primary tumor cells removed from a patient.

The term "autologous promoter" is intended to mean a 5' LTR of HERV-W, on the condition that it is functional, and the term "heterologous promoter" is intended to mean any promoter which does not belong to the HERV-W family, of viral, retroviral or cellular origin, optionally modified, on the condition that it is functional. Advantageously, the autologous or heterologous promoter is a strong promoter, i.e. it is capable of inducing quantitatively significant expression of the protein or of the polypeptide.

The fusogenic power of the Env HERV-W protein may also be used to promote the process of cell adhesion in the case of heterologous or homologous grafts or in cell repair processes.

Example 1

Cell Lines

The TELCeB6 line (Cosset et al., Journal of Virology, 69 (12): 7430-7436 (1995)) derives from the TELac2 line after transfection and clonal selection of an expression plasmid intended to produce Gag and Pol protein of the MoMLV (Moloney murine leukemia virus) type. The TELac2 line initially derives from human rhabdomyosarcoma cells TE671 (ATCC CRL 8805) and expresses the nlsLacZ retroviral reporter vector (Takeuchi et al., Journal of Virology, 68 (12): 8001-8007 (1994)). The production of infectious retroviral particles by TELCeB6 cells depends on the envelope expression vectors transfected.

The cells are cultured in DMEM medium (Dulbecco modified Eagle medium—Life Technologies) with 10% of fetal calf serum (Life Technologies). In general, this medium was used for all the other cell types, i.e. the TE671 (ATCC CRL 8805—human rhabdomyosarcoma), A-431 (ATCC CRL-1555—solid tumor, human epidermoid carcinoma), HeLa (ATCC CCL-2), COS (ATCC CRL-1651), PAE (pig aorta endothelial cells), XC (ATCC CCL-165—rat sarcoma), NIH-3T3 and QTB (ATCC CRL-1708) cells.

Construction of the Envelope Expression Vectors:

The pHCMV plasmid was used for the expression of env HERV-W. The FBASALF-ARless plasmid was used as a positive control for fusion; it produces a highly fusogenic form of the amphotropic MLV envelope glycoprotein, modified by introducing a stop codon before the first amino acid of the intracytoplasmic peptide p2-R (Rein et al., Journal of Virology, 68 (3): 1773-1781 (1994)). env HERV-W cloned, in the antisense direction, into the pHCMV plasmid was used as a negative control.

Transfection and cell-to-cell fusion tests (coculture): The envelope glycoprotein expression plasmids are transfected into the TELCeB6 cells by calcium phosphate precipitation (Cosset et al., Journal of Virology, 69 (10): 6314-6322 (1995)). The confluent TELCeB6 cells expressing Env are fixed with 0.5% glutaraldehyde in PBS, 24 h after transfection. Staining with May-Grünwald and Giemsa solutions (MERCK) is then carried out according to the supplier's recommendations. It stains the nuclei violet and the cytoplasms mauve and enables the syncytia to be visualized.

For the coculture experiments, the transfected cells are detached from the support, counted and then re-seeded at equal concentration ($3\times10^5$ cell/well) in 6-well plates. Fresh indicator cells are then added to the transfected cells, at $10^6$ per well, and the coculture is allowed to continue for 24 h. XGal (5-bromo-4-chloro-3-indolyl-β-D-galactopyranoside) staining may then be carried out in order to stain the nucleus of the TELCeB6 cells (Cosset et al., Journal of Virology, 69 (10): 6314-6322 (1995)). It is followed by staining with May-Grünwald and Giemsa solutions (MERCK), carried out according to the supplier's recommendations.

Most of the syncytia can be observed 18 to 24 hours after the beginning of transfection; the progressive detachment of the cells no longer allows observation or staining 36 hours after transfection. The fusion observed corresponds to a fusion "from within", i.e. a cell-to-cell fusion, based on a cell expressing the envelope, as opposed to a fusion "from without" which corresponds to formation of syncytia subsequent to a virion-cell(s) fusion.

Table I below gives the results obtained regarding the capacity for cell-to-cell fusion of Env HERV-W by direct transfection, compared to that of the ARless control envelope. The TELCeB6 and TE671 cells correspond to lines of human origin. The COS cells are green monkey kidney cells. The XC cells are rat cells.

TABLE I

| Envelope | fusion index[a] on | | | |
| --- | --- | --- | --- | --- |
| | TELCeB6 cells | TE671 cells | COS cells | XC cells |
| Arless | 33 | 8.6 | inn. | 40 |
| HERV-W | 61 | 24.7 | 36 | 0 |

[a]The fusion index corresponds to the percentage (N-S)/T, in which N is the number of nuclei in syncytia, S is the number of syncytia and T is the total number of nuclei counted. inn. signifies innumerable, organized in a "network".

Table I shows that the results for Env HERV-W are at least as good as for the control on the cells of human origin. They are less good on the simian cells. Env HERV-W does not induce the formation of syncytia on rat cells.

Table II below gives the data observed in experiments of coculturing indicator cells with TELCeB6 cells transfected with pHCMV-env HERV-W. The type, origin and species of the indicator cells are indicated. The formation of syncytia is indicated by the term yes/no.

TABLE II

| Species | Cell type | Origin | Fusion in coculture with TELCeB6 |
| --- | --- | --- | --- |
| Human | TE671 | Rhabdomyosarcoma | Yes |
| | A431 | Epidermoid carcinoma | Yes |
| | HeLa | Epitheliold carcinoma | Yes |
| Monkey | COS | Fibroblast type | Yes |
| Pig | PAE | Endothelium | Yes |
| Rat | XC | Sarcoma | No |
| Mouse | 3T3 | Fibroblastic | No |
| Quail | QT6 | Fibrosarcoma | No |

Table II gives the results of the coculture experiments as a function of the cell lines tested. Syncytia are observed in human rhabdomyosarcoma (TE671), epidermoid carcinoma (A431) and epithelioid carcinoma (HeLa) cells, and also in monkey cells of the fibroblast type (COS) and pig endothelium cells (PAE). The fact that the human endogenous envelope Env HERV-W is capable of fusing in pig cells may pose problems in the context of organ transplantation (xenotransplantation).

Example 2

Joint and then Selective Amplification of the LTR and of the Envelope

In order to study the polymorphism of the coding region of the envelope and of the associated 5' LTR U3 promoter region, located on chromosome 7, amplification specific for a 10 kb fragment is carried out using a pair of specific primers. In fact, given that the HERV-W family comprises many non-coding copies and in particular a considerable number of LTRs, this strategy makes it possible to specifically and jointly amplify the env region and its promoter sequence (5' LTR) located upstream, exclusively on chromosome 7. For this, use is made of a primer U6198 (SEQ ID NO:29) which hybridizes on a specific sequence located upstream of 5' LTR on chromosome 7, and a primer L6186 (SEQ ID NO:30) which hybridizes in an overlapping manner on the 3' LTR U5 region and the adjacent cellular gene, on this same chromosome. Long distance PCR (or LD-PCR) is carried out under the following conditions, 1×5 min at 94° C., 10×(10 sec at 94° C., 30 sec at 55° C., 8 min at 68° C.), 25×(10 sec at 94° C., 30 sec at 55° C., 8 min at 68° C.+10 sec/cycle), 1×7 min at 68° C., in the presence of amplification buffer (50 mM Tris HCL, pH 9.0, at 25° C., 15 mM $(NH_4)_2SO_4$, 0.1% Triton X-100); 1.5 mM $MgCl_2$, 0.25 mM of each dNTP, 330 nM of each primer (U6198 and L6186), 1U of DNA polymerase and also 200 ng of matrix (genomic DNA) in a final volume of 50 ml.

A nested "env" PCR and also a nested "LTR" PCR are carried out using this diluted 10 kb PCR product, in order to objectify the presence or absence of a polymorphism of these two regions. The dilution allows specific amplification from the LD-PCR product and not from the starting genomic material. The nested "env" PCR is carried out using the U6189 (SEQ ID NO:31) and L6186 (SEQ ID NO:30) primers, the U6189 primer being that used for the LD-PCR, the U6189 primer being located upstream of the env ATG. The 5' LTR U3 region is amplified with the U6460 (SEQ ID NO:32) and L5643 (SEQ ID NO:33) pair of primers. The U6460 primer hybridizes upstream of the 5' LTR, while the L5643 primer hybridizes in the R domain of the 5' LTR. The nested PCRs are carried out under the following conditions, 1×5 min at 94° C., 30×(1 min at 94° C., 1 min at 53° C., 3 min at 72° C.), 1×7 min at 72° C., in the presence of amplification buffer (10 mM Tris HCL, pH 8.3, 50 mM KCl), 1.5 mM $MgCl_2$, 0.25 mM of each dNTP, 330 nM of each primer, 1.25 U of DNA polymerase and an aliquot of the LD-PCR amplification product, in a final volume of 50 ml.

Analysis of the Polymorphism:

In order to objectify the presence or absence of a polymorphism, the nested PCR products can be analyzed in various ways, in particular sequencing or analysis by the SSCP (Single Strand Conformation Polymorphism) technique which makes it possible to demonstrate the presence of at least one mutation between two short sequences with a mean size of 250 bp.

Polymorphism of the env gene: the use of 20 primers (10 even sense primers: 6302 to 6320, SEQ ID NOs: 34, 36, 38, 40, 42, 44, 46, 48, 50 and 52, and 10 odd antisense primers: 6303 to 6321, SEQ ID NOs: 35, 37, 39, 41, 43, 45, 47, 49, 51 and 53) makes it possible to sequence the coding region of the envelope using the nested envelope PCR product. These primers may also be used for analysis of the polymorphism by SSCP. By way of example, the sequences of the envelope genes of three healthy donors labeled D6, D10 and D21, are illustrated in FIG. 2. These sequences show the existence of a low polymorphism rate. If the envelope sequence of donor D6 is used as an arbitrary reference, the sequence of the envelope of donor D21 has a mutation at position 386 (T386C), the replacement of the thymine with cytosine inducing an amino acid change of valine to alanine (V128A by protein numbering). Similarly, the sequence of the envelope gene of donor D10 has two mutations relative to the sequence of donor D6, at position 671 (T671C) and 920 (G920A), inducing two amino acid changes, from valine to alanine (V224A by protein numbering) and from serine to asparagine (S306N by protein numbering), respectively. These sequences illustrate the existence of a polymorphism. 12 patient DNAs were sequenced, which made it possible to observe a low polymorphism rate between the DNAs tested. For example, comparison of the sequences derived from two individuals, noted 10 and 21, shows the presence of a nucleic acid difference of three bases over the 1617 bases of the gene, which corresponds to a polymorphism rate of 0.19%. Two mutations are located on the sequence of DNA 10 (T671C and G920A) and one on the sequence of DNA 21 (T386C). The sequence of individual 6 is used as the reference. This same analysis at the protein level makes it possible to observe 3 mutated amino acids for the entire envelope comprising, in total, 538 amino acids, i.e. a polymorphism rate of 0.56%. The two mutations of the sequence derived from individual 10 are V224A and S306N, and that of the sequence derived from individual 21 is V128A.

Polymorphism of the LTR5' U3 promoter region associated with the envelope gene: the sequencing of the 5' LTR U3 domain is carried out using the 2 primers previously used for the nested LTR PCR. By way of example, the sequences of the 5' LTR U3 region (associated with the envelope gene) of two of the healthy donors (labeled D6 and D21), for which the envelope has, moreover, been sequenced, are illustrated in FIG. 3. These sequences show the existence of a polymorphism rate which is higher than for the envelope gene. The variations at positions 210 (T for D6, C for D21), 211 (G for D6, A for D21), 229 (A for D6, G for D21), 231 (T for D6, C for D21) and 232 (C for D6, A for D21) will in particular be noted.

The sequences of the primers used for the PCR, the SSCP and the sequencing are illustrated in table III below.

TABLE III

| NAME: | NUCLEOTIDE SEQUENCES: |
|---|---|
| | Long distance PCR primers |
| U6198 (SEQ ID NO:29): | 5'-CAA-AAC-GCC-TGG-AGA-TAC-AGC-AAT-TAT-C-3' |
| L6186 (SEQ ID NO:30): | 5'-GCA-CCC-TCA-TGG-TGG-TTG-TGT-TAC-TTG-G-3' |
| | Nested env PCR primers |
| U6189 (SEQ ID NO:31): | 5'-CTG-AAA-ATC-CAG-GAG-ACA-ACG-CTA-GC-3' |
| L6186 (SEQ ID NO:30): | 5'-GCA-CCC-TCA-TGG-TTG-TGT-TAC-TTG-G-3' |

TABLE III-continued

| NAME: | NUCLEOTIDE SEQUENCES: |
|---|---|
| | Nested 5' LTR PCR primers |
| U6460 (SEQ ID NO:32): | 5'-TTG-GTA-CCC-AAA-ACG-CCT-GGA-GAT-ACA-GCA-ATT-ATC-3' |
| L5643 (SEQ ID NO:33): | 5'-AAC-TCG-AGT-GAA-ATA-GCA-TGA-AAA-CAG-AG-3' |
| | SSCP and env sequencing primers |
| U6302 (SEQ ID NO:34): | 5'-AGG-AAA-GTA-ACT-AAA-ATC-ATA-AAT-C-3' |
| L6303 (SEQ ID NO:35): | 5'-GGT-TCC-CTT-AGA-AAG-ACT-CC-3' |
| U6304 (SEQ ID NO:36): | 5'-AAT-ATT-GAT-GCC-CCA-TCG-TAT-A-3' |
| L6305 (SEQ ID NO:37): | 5'-CCA-GTT-TGG-GTG-AAG-TAA-GTC-3' |
| U6306 (SEQ ID NO:38): | 5'-GGA-GGA-CTT-GGA-GTC-ACT-GTC-3' |
| L6307 (SEQ ID NO:39): | 5'-AGG-CGA-GTA-TGG-GTA-CGG-AG-3' |
| U6308 (SEQ ID NO:40): | 5'-GGA-CTA-GAT-CTC-TCA-AAA-CTA-CA-3' |
| L6309 (SEQ ID NO:41): | 5'-ACG-GAA-GTG-GTG-TTT-ATT-TCT-G-3' |
| U6310 (SEQ ID NO:42): | 5'-CCT-GAA-CAA-TGG-AAC-AAC-TTC-3' |
| L6311 (SEQ ID NO:43): | 5'-ATT-CCT-GAG-GGT-AGG-CAG-AC-3' |
| U6312 (SEQ ID NO:44): | 5'-GGT-AAC-TCC-TCC-CAC-ACA-AA-3' |
| L6313 (SEQ ID NO:45): | 5'-GAA-TGG-GTA-CTC-TTT-TGT-TGC-3' |
| U6314 (SEQ ID NO:46): | 5'-TAC-AGT-TAT-GTC-ATA-TCT-AAG-CC-3' |
| L6315 (SEQ ID NO:47): | 5'-TAA-GTT-GAT-CTT-GCA-AGG-TGA-C-3' |
| U6316 (SEQ ID NO:48): | 5'-CTA-AAT-GGG-GAC-ATG-GAA-CG-3' |
| L6317 (SEQ ID NO:49): | 5'-TAT-TCG-ATC-TGG-AAT-TTC-TTC-AAC-3' |
| U6318 (SEQ ID NO:50): | 5'-CAA-TCC-GGA-ATC-GTC-ACT-GA-3' |
| L6319 (SEQ ID NO:51): | 5'-AGA-CAA-AGT-TAA-CAA-GGA-GGT-TC-3' |
| U6320 (SEQ ID NO:52): | 5'-ACT-CCT-CTT-TGG-ACC-CTG-TAT-C-3' |
| L6321 (SEQ ID NO:53): | 5'-GAG-GTT-GGC-CGA-CCA-CCG-3' |

U refers to sense primers and L refers to reverse primers.

Example 3

Interference tests were carried out in order to determine the receptor recognized by the envelope glycoprotein of HERV-W among the receptors known to be expressed in human cells, i.e. PiT-2 (the receptor for amphotropic MLVs), PiT-1 (the receptor for GALV—gibbon ape leukemia virus and FeLV-B—feline leukemia virus type B) and hATB° (the receptor for type D mammalian retroviruses, also recognized by the RD114 retrovirus). For this, TELCeB6 cells were transfected either with the expression plasmid coding for the HERV-W envelope, with the expression plasmid expressing the antisense messenger RNA for the gene coding for the HERV-W envelope, or with the expression plasmid coding for a hyperfusogenic variant of the amphotropic MLV envelope named ARless. These cells, named "producer cells", were then cocultured with human cells, termed "indicator cells", expressing the receptor for the HERV-W envelope, and which also stably expressed either the envelope of GALV, the envelope of amphotropic MLV, or the envelope of RD114. The expression of these diverse envelope glycoproteins on these cells is capable of recognizing the corresponding receptors, of blocking them and therefore of decreasing their ability to interact with a retroviral envelope glycoprotein corresponding to them but expressed exogenously at the surface of the "producer" cells. Thus, if during the tests for fusion by coculturing a decrease is observed in the formation of syncytia for an indicator cell type which blocks one of these receptors compared to the parental indicator cell for which all of the three potential receptors are fully accessible, the nature of the receptor recognized by the envelope expressed on the producer cell may be deduced therefrom. After coculturing for two days, the cells are fixed and stained and the fusion indices determined. The results are given in table IV below.

TABLE IV

| Envelope protein expressed in the producer cells | Envelope proteins expressed in the indicator cells | | | |
|---|---|---|---|---|
| | Control | MLV-A | GALV | RD114 |
| Arless | + | − | + | + |
| HERV-W antisense | − | − | − | − |
| HERV-W | + | + | + | − |

− signifies a lack of syncytia and + signifies the presence of syncytia
Control signifies that there is no envelope protein expressed in this cell.

These results make it possible to deduce that the envelope glycoprotein of HERV-W recognizes the HATB° receptor for type D mammalian retroviruses. Specifically, although this envelope is fusogenic for the parental indicator cells or for the indicator cells expressing either the MLV-A envelope or the GALV envelope, no syncytia are observed when the producer cells expressing the envelope glycoprotein of HERV-W are cocultured with the indicator cells expressing the RD114 envelope.

Example 4

Control of the Fusogenic Activity of Env HERV-W by its Cytoplasmic Component

The involvement of the cytoplasmic component of Env HERV-W in the fusogenic activity of this glycoprotein is demonstrated by the construction and characterization of the following recombinant glycoproteins:

W/CD46+, derived from human CD46, a factor protecting cells against complement and not involved in the formation of syncytia, comprising the ectodomain and the transmembrane domain of Env HERV-W (aa 1 to 469) fused to the cytoplasmic domain of CD46 (aa 335 to 369). This chimeric molecule is not fusogenic in a cell-cell fusion test (FIG. 5).

W/R+, derived from the envelope glycoprotein of the MLV-A (amphotropic murine leukemia virus) retrovirus, nonfusogenic when expressed independently of the other proteins of MLV-A, comprising the ectodomain and the transmembrane domain of Env HERV-W (aa 1 to 469) fused to the cytoplasmic domain of the envelope glycoprotein of the MLV-A retrovirus (aa 622 to 654). This chimeric molecule is not fusogenic in a cell-cell fusion test (FIG. 5).

RD/W, derived from the envelope glycoprotein of the RD114 feline endogenous retrovirus, nonfusogenic when expressed independently of the other proteins of RD114, comprising the cytoplasmic domain and the transmembrane domain of Env HERV-W (aa 448 to 538) fused to the ectodomain of the envelope glycoprotein of the RD114 retrovirus (aa 1 to 508). This chimeric molecule is fusogenic in a cell-cell fusion test (FIG. 5).

The attached FIG. 5 represents the scheme and characterization of the abovementioned Env HERV-W chimeras and the results obtained in a cell-cell fusion test.

The ectodomain of Env HERV-W is defined by the polypeptide derived from the protein precursor containing amino acids (aa) 21 to 447; the transmembrane domain, aa 448 to 469 and the cytoplasmic component, aa 470 to 538 (Blond et al., (1999), Molecular characterization and placental expression of HERV-W, a new human endogenous retrovirus family. Journal of Virology. 73:1175-1185).

The ectodomain of CD46 is defined by the polypeptide derived from the protein precursor containing amino acids (aa) 35 to 312; the transmembrane domain, aa 313 to 334 and the cytoplasmic component, aa 335 to 369 (Yant et al., (1997), Identification of a cytoplasmic Tyr-X-X-Leu motif essential for down regulation of the human cell receptor CD46 in persistent measles virus infection. J. Virol. 71:766-770).

The ectodomain of Env MLV-A is defined by the polypeptide derived from the protein precursor containing amino acids (aa) 32 to 598; the transmembrane domain, aa 599 to 621 and the cytoplasmic component, aa 622 to 654 (Ott and Rein, (1990), Sequence analysis of amphotropic and 10A1 murine leukemia virus: close relationship to mink cell focus forming viruses. J. Virol. 64:757-766).

The ectodomain of Env RD114 is defined by the polypeptide derived from the protein precursor containing amino acids (aa) 18 to 508; the transmembrane domain, aa 509 to 530 and the cytoplasmic component, aa 531 to 564 (Cosset et al., (1995b), High titer packaging cells producing recombinant retroviruses resistant to human serum. J. Virol. 69:7430-7436).

SU signifies surface subunit: TM transmembrane subunit; SP signal peptide; tm transmembrane anchoring domain; cyt cytoplasmic component; RBD receptor-binding domain; PRR proline-rich region; C carboxy-terminal domain of the SU.

---

The invention claimed is:

1. A method for detecting whether an interaction occurs between a polypeptide of a producer cell and a neutral amino acid transporter cell surface receptor of an indicator cell ex vivo or in vitro, wherein the polypeptide has a sequence which consists of SEQ ID NO:1, said method comprising:
contacting said indicator cell with said producer cell;
observing formation of syncytia between said producer cell and said indicator cell or non-formation of syncytia between said producer cell and said indicator cell; and
correlating said formation of syncytia with occurrence of an interaction between the polypeptide of the producer cell and the neutral amino acid transporter cell surface receptor of said indicator cell or correlating said non-formation of syncytia with a lack of an interaction between the polypeptide of the producer cell and the neutral amino acid transporter cell surface receptor of said indicator cell.

2. The method of claim 1, wherein said receptor is the hATB° receptor for type D mammalian retroviruses.

3. The method of claim 1, wherein said indicator cell is a cancer cell.

4. The method of claim 1, wherein said indicator cell is a cell of human origin.

5. The method of claim 1, wherein said method comprises correlating the formation of syncytia with expression of the polypeptide on the surface of the producer cell.

6. The method of claim 1, wherein said producer cell is selected from the group consisting of bone cells, muscle cells, placenta cells, endothelial cells, epithelial cells, glial cells, tumor cells, and cells derived from tumor cell lines.

7. The method of claim 1, wherein said producer cell is a cell from a blood vessel.

8. The method of claim 1, further comprising testing effectiveness of or selecting medicinal substances, drugs or gene/prodrug systems by said method by contacting said producer cells with medicinal substances, drugs or gene/prodrug systems and determining the effect of said medicinal substances, drugs or gene/prodrug systems on said formation or non-formation of syncytia.

9. The method of claim 1, further comprising obtaining said producer cell by transfecting a cell with a vector comprising a gene encoding said polypeptide and a promoter for expressing said polypeptide.

10. The method of claim 9, wherein said promoter is a heterologous promoter.

11. The method of claim 9, wherein said promoter is an autologous promoter.

12. The method of claim 1, wherein said contacting is conducted at a neutral pH.

13. The method of claim 8, further comprising selecting a medicinal substance, drugs or gene/prodrug system candidate based on occurrence of an interaction between the polypeptide of the producer cell and the neutral amino acid transporter cell surface receptor of said indicator cell.

\* \* \* \* \*